United States Patent [19]

Eydelman

[11] Patent Number: 4,525,775
[45] Date of Patent: Jun. 25, 1985

[54] ADAPTIVE CONTROL SYSTEM

[76] Inventor: Grigory Eydelman, 141 St. Paul's Pl., West Hempstead, N.Y. 11552

[21] Appl. No.: 438,381

[22] Filed: Nov. 1, 1982

[51] Int. Cl.³ ............................................. G06F 15/42
[52] U.S. Cl. .................... 364/148; 128/672; 364/415
[58] Field of Search ............... 364/148, 413, 415, 513; 128/670, 671, 672, 687, 700, 710; 604/65, 66, 67, 50

[56] References Cited

U.S. PATENT DOCUMENTS

| | | | |
|---|---|---|---|
| 3,601,811 | 8/1971 | Yoshino | 364/148 X |
| 3,814,082 | 6/1974 | Taylor | 128/670 |
| 3,996,928 | 12/1976 | Marx | 128/671 |
| 4,053,951 | 10/1977 | Hudspeth et al. | 128/670 X |
| 4,404,974 | 9/1983 | Titus | 128/670 |
| 4,417,306 | 11/1983 | Citron et al. | 364/415 |

Primary Examiner—Joseph Ruggiero
Attorney, Agent, or Firm—Lackenbach Siegel Marzullo Presta & Aronson

[57] ABSTRACT

An adaptive control system incorporating self-teaching and self-programming features senses a pair of input signals for providing an output control signal. In a medical situation, the output signal drives a medicine delivery system in response to the sensing of a precursor signal and a condition signal which represent the future and the present states of a patient's health. Memory is provided in the form of a set of integrators which accumulate quantities of data representing the joint occurrence, during a measurement interval, of the precursor and the condition signals as quantized into preset ranges of values. Generation of the output signal is based on the amount of stored data as well as on the presence of a condition signal indicating a hazardous condition. Circuitry is provided for the selective incrementing and decrementing of the contents of the integrators in a manner analogous to the encouragement and punishment in a learning process.

26 Claims, 32 Drawing Figures

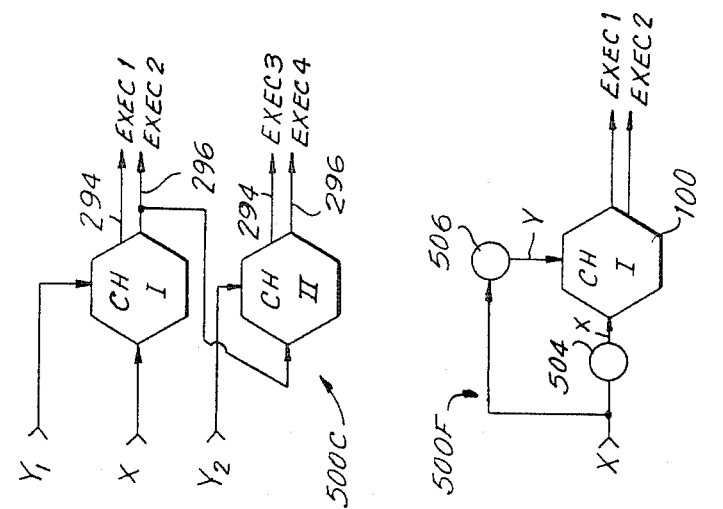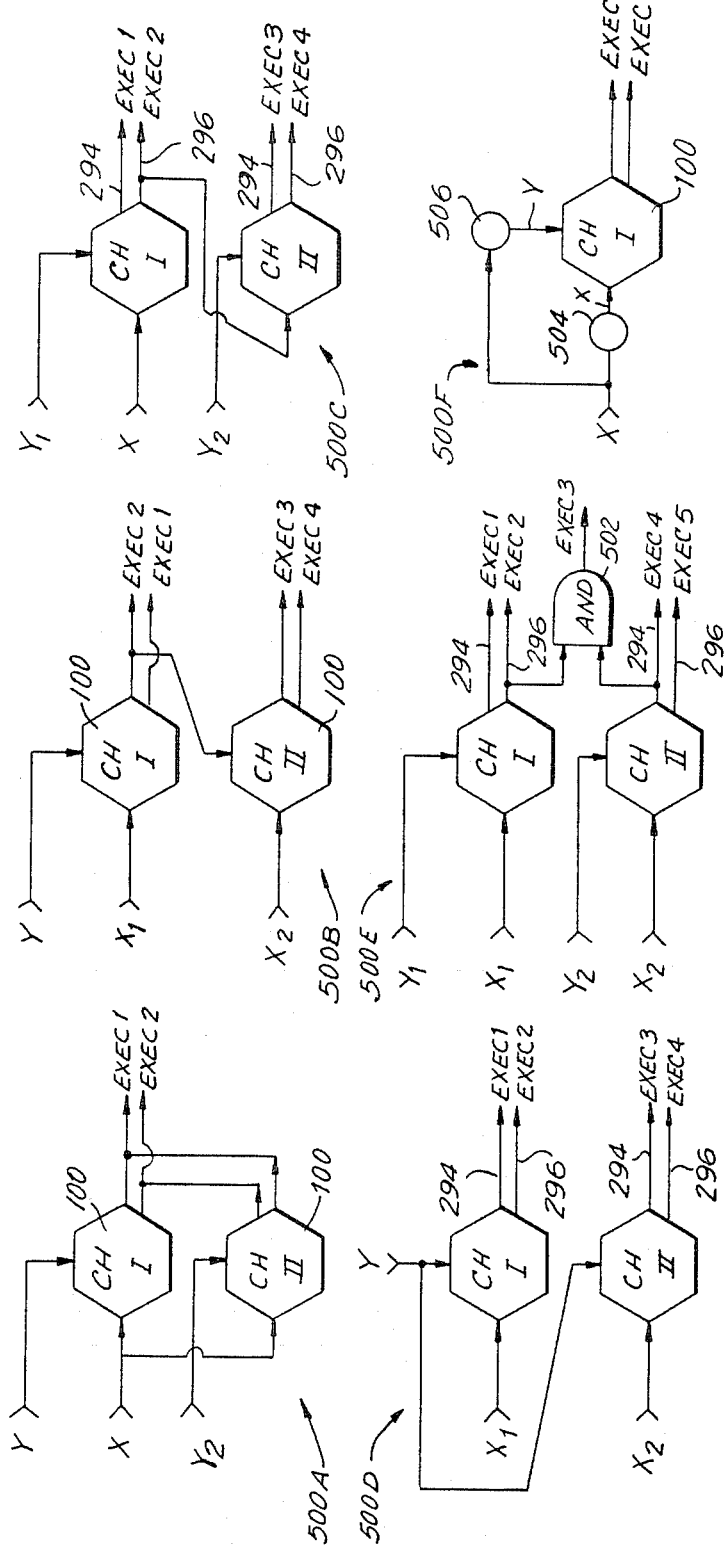

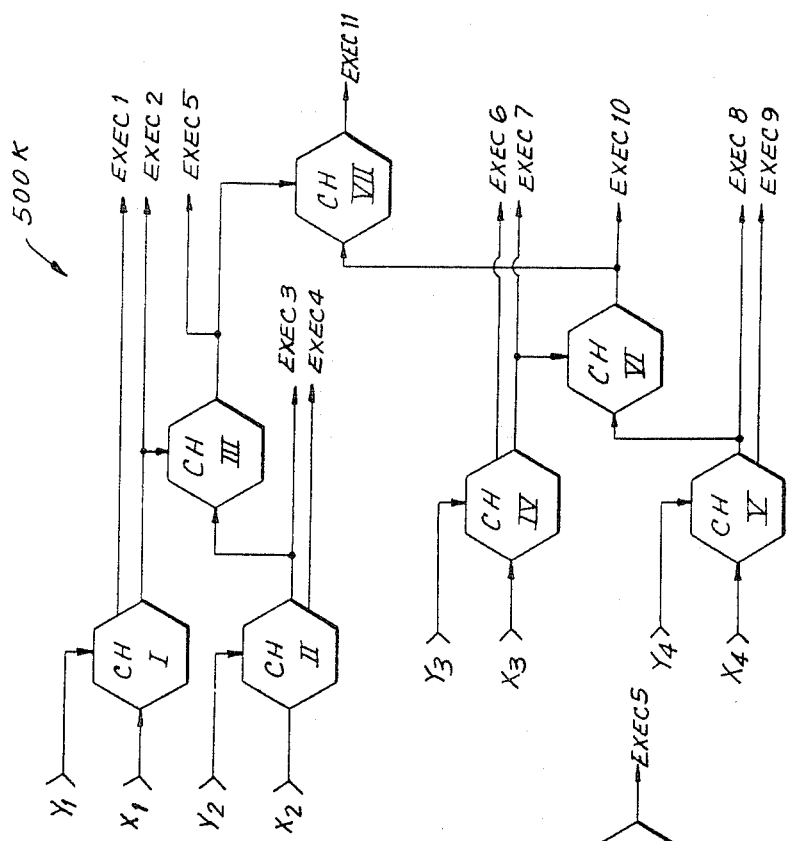
FIG. 21K
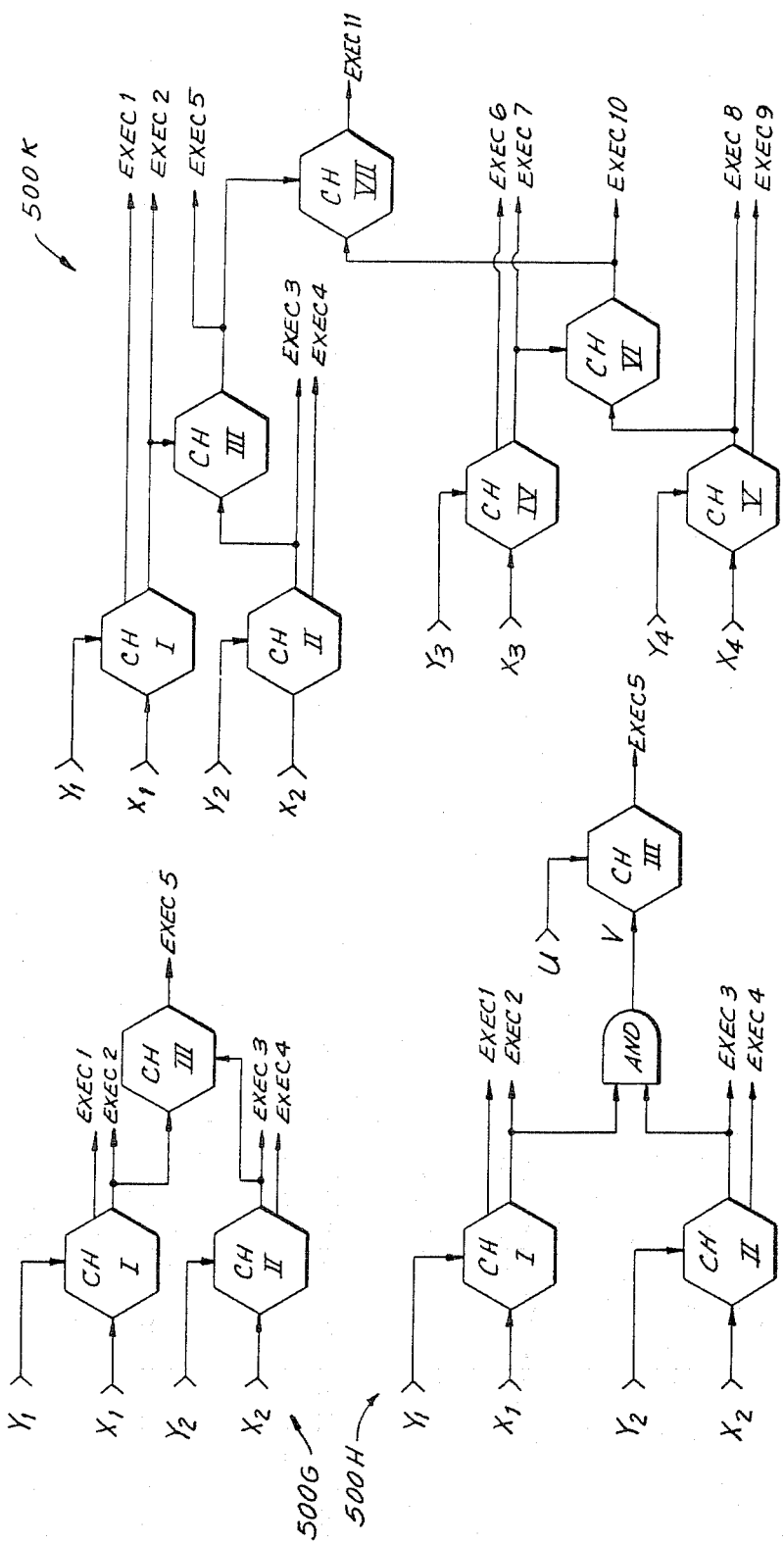
FIG. 21G
FIG. 21H

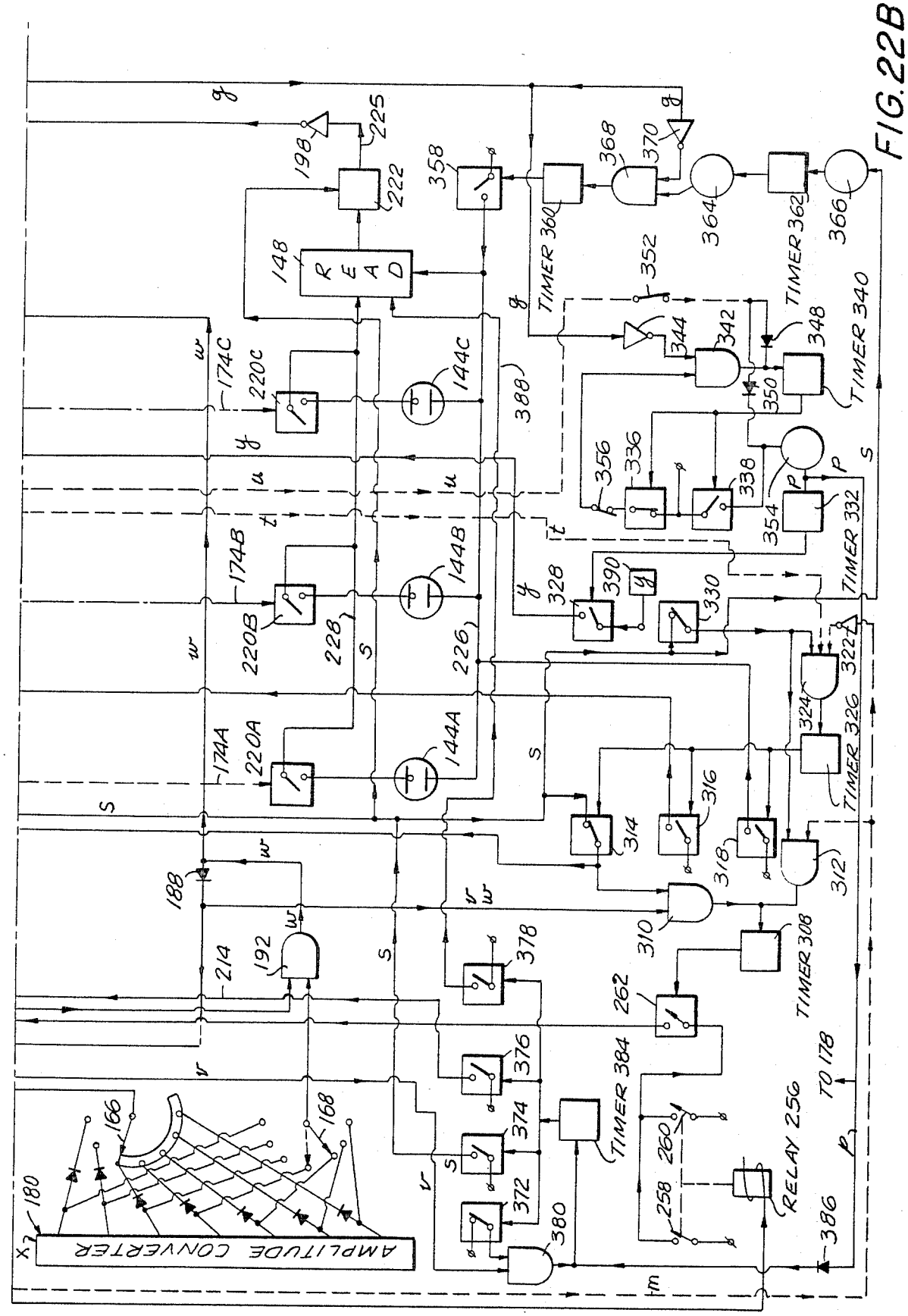

ADAPTIVE CONTROL SYSTEM

BACKGROUND OF THE INVENTION

This invention relates to control systems and, more particularly, to a system correlating events among paired variables, and wherein such correlation is retained for varying retention times depending on the course of successive events.

Control systems are widely used today in a broad class of physical systems ranging from the control of elevators to the pumping of oil, in the control of chemical processes, and in electronic systems such as radar and communications. Research is being conducted for the implementation of control in biological systems. Increased versatility for the control systems is attained by the introduction of programmable features such as those associated with the use of a computer as a component of the control system. Thereby, the operation of the system can be altered as required by a specific situation by a corresponding change in the computer program. Incrased capability for the control systems is attained by the introduction of adaptive features such as may be found, for example, in an adaptive radar antenna wherein the response of the antenna is made to vary in accordance with the characteristics of a signal incident upon the antenna. Yet another feature which has been studied in systems having a "learning" capability is a self-programmable feature wherein the program can be varied in accordance with measured changes in input variables to the system.

By the use of the foregoing features, control systems can be constructed with increased versatility and capacity for handling situations of ever increasing complexity. But, such capability is attained at a cost, namely, with increased capability there is a corresponding increase in the complexity and expense of the equipment of the control system.

A problem arises in that there are many situations in which there is no room for complex, bulky and heavy equipment. Thus, the foregoing control systems incorporating the adaptive and self-programmatic features would not be suitable in a health care device wherein such a system is to be worn by a person for the control of a bodily function. And even in situations wherein there may be room for such equipment, the expense both in terms of money and in terms of the engineering manpower required to operate the equipment militates against the use of the foregoing control systems.

A further problem arises in the case of programmed equipment for use in the care of physiological phenomena in human patients. Due to individual variations among people, a program adapted for use with one patient has been found to be substantially inoperative with respect to other patients.

SUMMARY OF THE INVENTION

The foregoing problems are overcome and other advantages are provided by a system incorporating the invention to provide versatility and capability associated with adaptive and self-programmatic systems to attain an adaptive control function within a relatively compact equipment package useful in both physiological control of living organisms and in the control of physical systems.

The most adaptive and capable control system is found in the human being. As is well known, a person is able to learn from a wide variety of experiences, is able to assess a situation to make the correct response, and is capable of implementing a host of activities from the steering of a car to the construction of a house. Accordingly, this invention borrows from the human learning experience, instead of employing the complex bulky equipment associated with computer systems and their peripheral equipments to provide a highly capable and adaptive control system with a self-teaching feature, all accomplished with a minimal amount of circuitry that is readily portable.

While the invention is useful both for the control of physical systems and biological systems, the preferred embodiment of the invention has been designed for the control of biological systems, more particularly, human beings and laboratory animals. The invention is most readily explained by considering a specific control situation, such as the control of the blood pressure in a person. Thus, one of the variables which is to serve as an input to the control system of the invention is a signal representing the blood pressure and, hence, the condition of the person. For convenience, this condition signal will often be referred to as the variable X.

In accordance with the theory of operation of the invention, a second input variable, Y, is to be applied to the control system of the invention, the variable, Y, being a signal which, in accordance with known biological phenomena, serves as a precursor of the variable, X. For example, let it be assumed that in certain medical situations, an excessive rise of the blood pressure into a danger zone (wherein the person's health becomes precarious) is preceded by a rise in the pulse rate, and wherein a drop in the pulse rate indicates that the health situation is improving such that the blood pressure will be returning to the normal range. Then the pulse rate is advantageously utilized as the precursor variable, Y. It is assumed, of course, that suitable electronic sensors of the blood pressure and the pulse rate would be attached to the person's body for the generation of the electric signal representations of the X and Y variables.

In the monitoring of the foregoing variables, the system benefits from the use of a threshold for dividing the possible range of blood pressure into two zones, namely, a zone of normal pressure, and a danger zone for all pressures above the threshold. In addition, a relatively narrow border zone is employed for sensing pressure immediately below the threshold. With respect to the monitoring of the pulse rate, several (or more) ranges of values of the rate are observed, the ranges being selected for known values of significant pulse rate. The foregoing constitutes the complete set of all values of X and Y which are to be utilized in the operation of the system. The determination of the foregoing values of X and Y is accomplished by the use of sets of window comparators.

In the processing of the data of the X and the Y variables, circuitry is provided for noting the occurrence of two successive appearances of the same value of the Y variable. Also, integrators are employed for storing a history of paired evehts, namely, the occurrences of values of X with corresponding values of Y. The magnitude of the signal accumulated in an integrator is a measure of correlation between the paired events. The foregoing correlations of the paired events, and the repetitions, or lack of repetitions, of the Y variable serve as a basis upon which further logic operations of the control system are based.

Further circuitry is employed for modifying the magnitudes of the signals accumulated in the integrators in a manner corresponding to the human learning process. Thus, circuits, to be referred to as encouragement and punishment circuits, are provided for incrementing and decrementing the magnitudes of the signals accumulated in the integrators in accordance with the success, or lack of success, obtained in the treatment of the person.

The system includes two output mechanisms which are executed for the administration of medication, or other form of therapy such as electric shock, for the treatment of the person. For example, the mechanisms may include storage flasks of the medications with valving for metering the medications from the respective flasks via tubing to the person for intravenous administration of the medications. One of the mechanisms administers a very small quantity of the medication to the person for test purposes while the second mechanism provides the normal dosage as would be utilized for correction of the harmful situation such as the reduction of the foregoing high blood pressure. The encouragement and punishment circuits operate in response to observed beneficial or deleterious effects on the person resulting from the foregoing administrations of the medication.

The system further comprises readout units for reading out data stored in the integrators. Each reading out of data is accompanied by a decrementing of the magnitude of the signal accumulated in an integrator. This decrementing corresponds to the human learning experience wherein continued response to a stimulus without reinforcement results in a reduction in the drive to respond further. Thereby the implementation of the system of the invention follows the learning mechanisms of the human body.

BRIEF DESCRIPTION OF THE DRAWINGS

The foregoing aspects and other features of the invention are explained in the following description taken in connection with the accompanying drawings wherein:

FIGS. 21A-21L show the use of the system of FIG. 1 as a building block in the construction of networks of these systems resulting in composite systems having the capacity to handle situations involving multiple inputs and multiple outputs; and FIGS. 22A-22B taken together provide an overall schematic diagram of the electronic circuitry set forth in the FIGS. 2-15, the elements of the FIGS. 22A-22B having appeared previously in the FIGS. 2-15, with some of the connecting lines being shown as dashed lines for increased legibility.

DESCRIPTION OF THE PREFERRED EMBODIMENT

Figure 1:
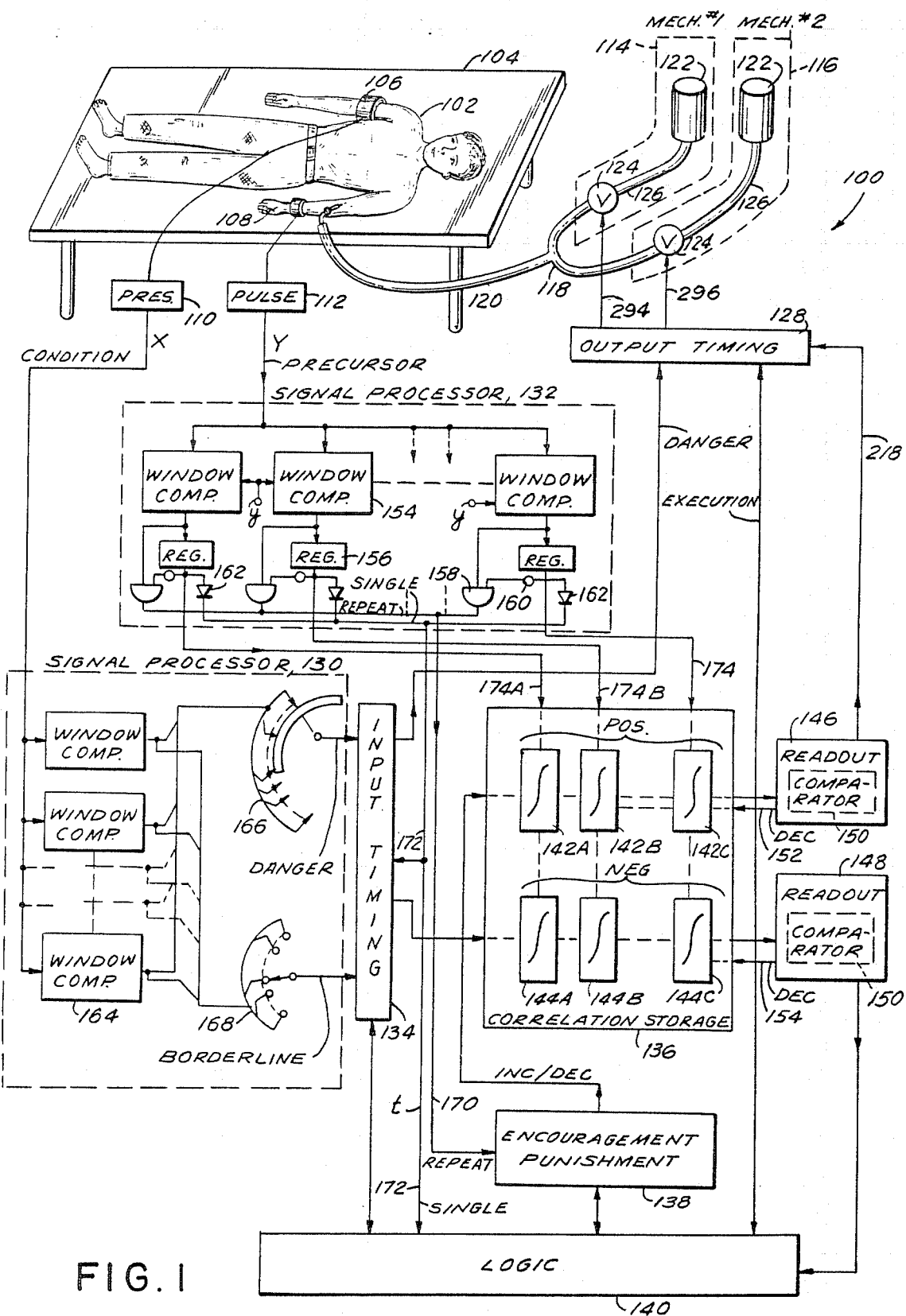
FIG. 1 is a simplified block diagram of the invention shown in use in the monitoring and treatment of a human patient.

Referring now to FIG. 1, there is shown a system 100 incorporating the invention and being coupled electrically to a human patient 102 for monitoring his vital signs and for taking corrective action, by the administration of medication, in the event that any danger condition is detected. The patient 102 is shown lying on a table 104 with a detector 106 of blood pressure affixed about his right arm in the form of a cuff, and with a detector 108 of the pulse rate affixed above his left wrist in the form of a cuff. A sending unit 110 connects with the detector 106 for developing an electric signal having an amplitude dependent on the blood pressure. A sending unit 112 connects with the detector 108 for developing an electric signal having an amplitude dependent on the pulse rate. Such detecting and sending units are well known and are presently employed in the intensive care units of hospitals. First and second mechanisms 114 and 116 for the dispensing of medication are joined together at a junction 118 and are coupled therefrom via a tube 120 to an arm of a patient 102 for the dispensing of the medication to the patient 102. Each of the mechanisms 114 and 116 includes a flask 122 and a valve 124 coupled to the flask 122 via a tube 126, output ports of the valves 124 being coupled via tubing to the junction 118. The valves 124 are electrically operated in response to electric signals provided by an output timing circuit 128.

The output signal of the sending unit 110, shown as X in the drawing, is representative of the condition of the patient 102, the signal being a measure of the blood pressure of the patient 102. The output signal of the sending unit 112, shown as Y on the drawing, serves as a precursor of the patient's condition, the signal being representative of the pulse rate of the patient 102. By way of example in the use of the system 100, it is presumed that the patient 102 is suffering from an ailment wherein his blood pressure may rise from a safe region wherein the pressure is relatively low to a dangerous region wherein the pressure is excessively high. It is furthermore assumed, with respect to this ailment, that the pulse rate tends to vary in a manner related to the blood pressure, namely, that the pulse rate tends to increase prior to an increase in the blood pressure and that, furthermore, the pulse rate tends to drop prior to a dropping of the blood pressure. Thus, by monitoring the precursor signal of the sending unit 112, a determination can be made as to whether the blood pressure will be rising or falling. Furthermore, in the administration of medication from the mechanisms 114 and 116, a determination can be made as to the effectiveness of the medication, which medication is intended to control the blood pressure so as to maintain it within a safe region. By observation of the precursor signal of the sending unit 112, the determination as to the effectiveness of the medication can be obtained prior to a significant change in the blood pressure since the pulse rate will change prior to the occurrence of a significant change in the blood pressure. In addition, it is noted that the absence in any change of the precursor signal upon the successive applications of medication would indicate that the medication is ineffective for altering the blood pressure and, accordingly, the administration of such medication should be terminated.

It is noted that the foregoing ailment of the patient 102 and the monitoring of the two body functions of blood pressure and pulse rate serve as one example in the use of the system 100. Some other form of ailment or condition of the patient 102 might be present by way of alternative example in the use of system 100. wherein eye movement might be regarded as a precursor signal while the body temperature would be ragarded as a signal of the condition of the patient 102. It is also noted that all input signals to the system 100, from the sending units 110 and 112, are electric signals, and that all output signals of the system 100, to the valves 124, are electric signals so that, insofar as the operation of the system 100 is concerned, the system 100 may be connected to a subject other than the patient 102. For example, such other subject might be another form of living organism such as a dog or cat. In addition, in the event that there would be a mechanical system for which a condition signal and a precursor signal be available, then the system 100 could also be utilized in the control of such mechanical system.

Again, with reference to the foregoing example wherein the patient 102 is being monitored during the administration of the medication, the condition signal, X, is processed by a signal processor 130, and the precursor signal, Y, is processed by a signal processor 132. Output signals of the processor 130 are coupled via an input timing circuit 134 to the output timing circuit 128 and also to a correlation storage unit 136. Output signals of the signal processor 132 are also coupled via the input timing circuit 134 to the correlation storage unit 136, as well as to an encouragement/punishment unit 138 and a logic circuit 140. As will be explained subsequently, the correlation sotrage unit 136 comprises two sections, one section comprising a set of integrators 142 for the positive correlation and a set of integrators 144 for the negative correlation. The integrators 142. and 144, as well as connecting circuit elements, are further identified by the legends A, B and C to facilitate identification of individual ones of the integrators 142 and 144. The integrators 142 for the positive correlation provide electric signals which are read out by a readout unit 146, the signals of the integrators 144 for the negative correlation being read out by a readout unit 148. Each of the readout units 146 and 148 include a comparator 150 so as to be responsive only to signals of the integrators 142 and 144 which are larger than preset reference signals applied to the comparators 150. Output signals of the readout units 146 and 148 are applied, respectively, to the timing circuit 128 and the logic circuit 140.

The use of the integrators 142 and 144 in the correlation storage unit 136 provides an operational characteristic to the system 100 which follows that associated with a human learning experience. Thus, as is well known, the response of a human being is reinforced in an experimental situation wherein a person receives a reward or other desired result in response to actions which he takes. Such a situation corresponds to a positive correlation between the results which are observed by the person and the actions which he takes to produce the results. On the other hand, in the event that the anticipated results are not obtained, any reinforcement which might have been previously obtained is decreased and may result in a negative reinforcement, corresponding to a negative correlation in such situations wherein a desired result is not obtained in response to the actions taken by the person. As will be seen in the ensuing description of the system 100, the integrators 142 of the positive correlation receive increments in their stored signals when desired results are obtained by the system 100 in response to the activation of the output signals of the timing circuit 128. In the absence of such desired results, the values of the stored signals in the integrators 142 decrease. Also, with respect to the integrators 144 of the negative correlation, an increase in the value of the stored signals occurs during situations of negative correlation or negative reinforcement, such being the case when the blood pressure remains in the normal zone and no useful result could be obtained in response to activation of the output signals of the output timing circuit 128. The magnitudes of the signals stored in the integrators 144 are found to decrease when, during abnormal blood pressure, the precursor signal changes in response to the activation of the output signals of the output timing circuit 128.

A further feature in the construction of the system 100, to provide further similarity between the operation of the system 100 and the operation of a person in a learning experience, is found in the connection between the readout unit 146 and the integrators 142 of the positive correlation, as well as in the connection of the readout unit 148 and the integrators 144 of the negative correlation. Thus, via lines 152 and 154 from the readout units 146 and 148, respectively, there are provided signals to the integrators 142 and 144, respectively, for decreasing the magnitudes of the signals stored therein. Such a decrement in the stored signals occurs during each readout of the respective signals of the integrators. The decrement in the signal magnitude is smaller than the increment which would occur upon the occurrence of a positive correlation in the case of the integrators 142, or a negative correlation, in the case of the integrators 144. Such decrementing of the stored values corresponds to the learning experience wherein a person does not receive an expected result in response to repeated actions on his part, in which case the reinforcement which he may have previously received is found to decrease. Eventually, the reinforcement would disappear. By providing for a small decrementing of the magnitude of the signals stored in the integrators 142 and 144, the readout units 146 and 148 automatically provide for the reduction in positive and negative reinforcement, the decrementing of the stored signals thus reducing the corresponding correlation to zero after many actions on the part of the system 100 without the attainment of the desired results.

The encouragement/punishment unit 138 provides yet another feature in the operation of the system 100 which parallels that of the human learning experience. The unit 138 is coupled only to the integrators 142 of the positive correlation and provides both for an incrementing and a decrementing of the magnitude of the signals stored in the integrators 142. With each favorable response of the patient 102 to the application of a dose of medicine from one of the mechanisms 114 and 116, the unit 138 increments the magnitude of the signal stored in the integrators 142. In the event of the occurrence of an unfavorable result, which unfavorable result would be indicated by a lack of change in the pulse rate of the precursor signal, namely, a repetition of the same amplitude of precursor signal from the implementation of one medicine dose to the next medicine dose, the unit 138 decrements the magnitude of the signals stored in the integrators 142.

The signal processor 132 comprises window comparators 154, registers 156, AND gates 158, delay units 160, and diodes 162. The signal processor 130 comprises window comparators 164, and selector switches 166 and 168. Each of the window comparators 154 and 164 may comprise a well-known circuit (not shown), for example, a first comparator which provides a logic 1 signal at the comparator output terminal when the comparator input signal is greater than a first reference value, a second comparator providing an output logic 1 signal when the foregoing input signal is less than a second reference value, and wherein both of the output signals are applied to an AND gate to attain the desired output signal of a window comparator. Thus, each window comparator provides an output logic 1 signal when the input signal falls within a predetermined range of values. For signals outside that range of values, wherein the signal amplitude is either greater or less than the range of values, the window comparator outputs a logic 0 signal. While only three window comparators 154 are shown in the processor 132, and while only three window comparators 164 are shown in the processor 130, it is to be understood that many more of these comparators may be utilized, for example, ten or twenty window comparators as required to adequately monitor the vital signs of the patient 102. In addition, when many of the window comparators are utilized, the foregoing range of values for each of the window comparators is made correspondingly smaller to provide for finer resolution of variations in the amplitudes of the condition and precursor signals of the sending units 110 and 112.

By way of alternative embodiments, it is noted that the set of window comparators 154 of the processor 132, as well as the set of window comparators 164 of the processor 130, may be fabricated as a well-know analog-to-digital converter (not shown) for quantizing the input analog signal to any one of a set of digitized values. For example, a decoder could be coupled to the start output terminal of the analog-to-digital converter to convert the digitally formatted signal to the set of separate lines, each of these lines corresponding to an output terminal of one of the window comparators 154 or 164. Also, such converters are available both in linear form and in nonlinear form, exponential and logarithmic forms being commercially available. In the nonlinear forms, the foregoing ranges of values would differ in extent from each other and, accordingly, it is to be understood that the comparators 154, as well as the comparators 164, may be provided with differing extents of their ranges of values.

In the processor 130, output terminals of individual ones of the window comparators 164 are coupled to corresponding input terminals of the switch 166 and of the switch 168. The switch 166 is constructed with a sliding contact for simultaneously connecting a preselectable set of the input terminals to the output terminal of the switch 166, the output circuits of the comparators 164 being understood to include diodes enabling the simultaneous connection of the output terminals of a plurality of the comparators 164 via the switch 166 to the output terminal of the switch 166. The output terminal of the switch 168 is selectably coupled to only one of the comparators 164.

In the operation of the signal processor 130, the switches 166 and 168 are set so that no output signals of the processor 130 are applied to the input timing unit 134 when the blood pressure of the patient 102 is in the safe region. The switch 166 is set to couple comparator signals to the timing unit 134 for all values of the condition signal of the pressure sending unit 110 corresponding to excessively high, unsafe blood pressure. Thus, a logic 1 in the output signal of the switch 166 designates a danger condition in the blood pressure of the patient 102. In the switch 168, connection is made to the comparator 164 having the range of values immediately below the threshold of the foregoing danger zone, a logic 1 in the output signal of the switch 168 thereby designating the presence of a blood pressure falling within a relatively narrow border zone between the safe and unsafe regions of blood pressure.

The foregoing operation of the signal processor 130 is in accordance with an important feature of the invention wherein the system 100 is able to function based on only two representations of the condition of the patient, namely, that the condition is dangerous or borderline.

In the signal processor 132, the comparators 154 are triggered by a trigger signal, y, to sample the precursor signal of the sending unit 112, the resulting sample appearing at the output terminal of the one comparator 154 having the range of values which includes the amplitude of the precursor signal. The sample is stored in the corresponding one of the registers 156, and is also applied to an input terminal of the corresponding AND gate 158. As will be described subsequently, a register 156 stores the value of the sample for a period of time until just before the next sample is to be taken. By means of the additional delay provided by a delay unit 160, the foregoing sample is applied to the other input terminal of the AND gate 158 at the same time that a later sample appears at the first input terminal of the foregoing AND gate 158, or of another of the AND gates 158. In the event that two sequentially occurring samples have the same value, then the AND gate 158, to which these two samples have been applied, signals the occurrence of the two equal samples. In the event that subsequent samples differ in amplitude, then there is no such signalling by any of the AND gates 158 of a repeating value of sample. The output terminals of the AND gates 158 are coupled together, via well-known diode steering logic (not shown), on line 170 to signal the occurrence of a sample repetition. The output terminals of the registers 156 are also coupled together via the diodes 162 to line 172 to signal the occurrences of each and every sample via a logic 1 signal on the line 172. Furthermore, the respective registers 156 are also coupled to the correlation storage unit 136 via lines 174 individual ones of which are further identified by the legends A, B. and C.

The foregoing operation of the signal processor 132 is in accordance with a further feature of the invention based on a single occurrences and repeat occurrences of the samples of the precursor signal. The operation of the encouragement/punishment unit 138 is dependent on the repeat signal of line 170.

In accordance with yet a further feature of the invention, the correlation is accomplished separately for each range of values of the precursor signal; thus, there is separate correlation for the signal sample of each window comparator 154. For each comparator 154, there are provided two integrators 142 and 144, the integrator 142 being employed for the positive correlation and the integrator 144 being employed for the negative correlation. For example, positive correlation, subject to certain constraints to be described, occurs upon the joint occurrence of an output danger-zone signal from the condition signal processor 130 with an output signal of the precursor signal processor 132. The negative correlation, subject to certain constraints to be described occurs in the absence of the output signal of the condition signal processor 130. Further details for both forms of correlation will be described subsequently.

Figure 2:
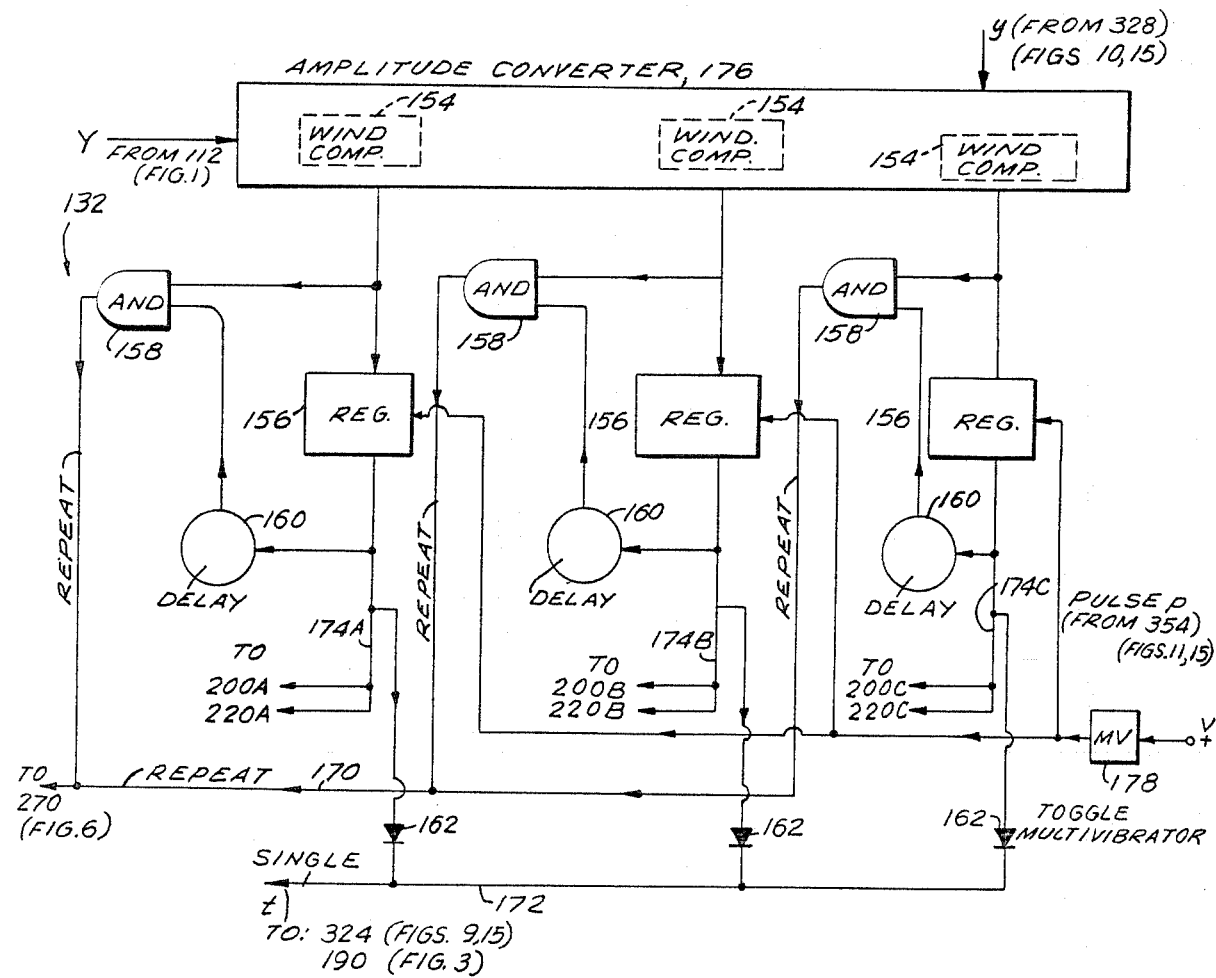
FIG. 2 is a schematic diagram of a signal processor of FIG. 1 for processing a precursor signal.
Figure 22A:
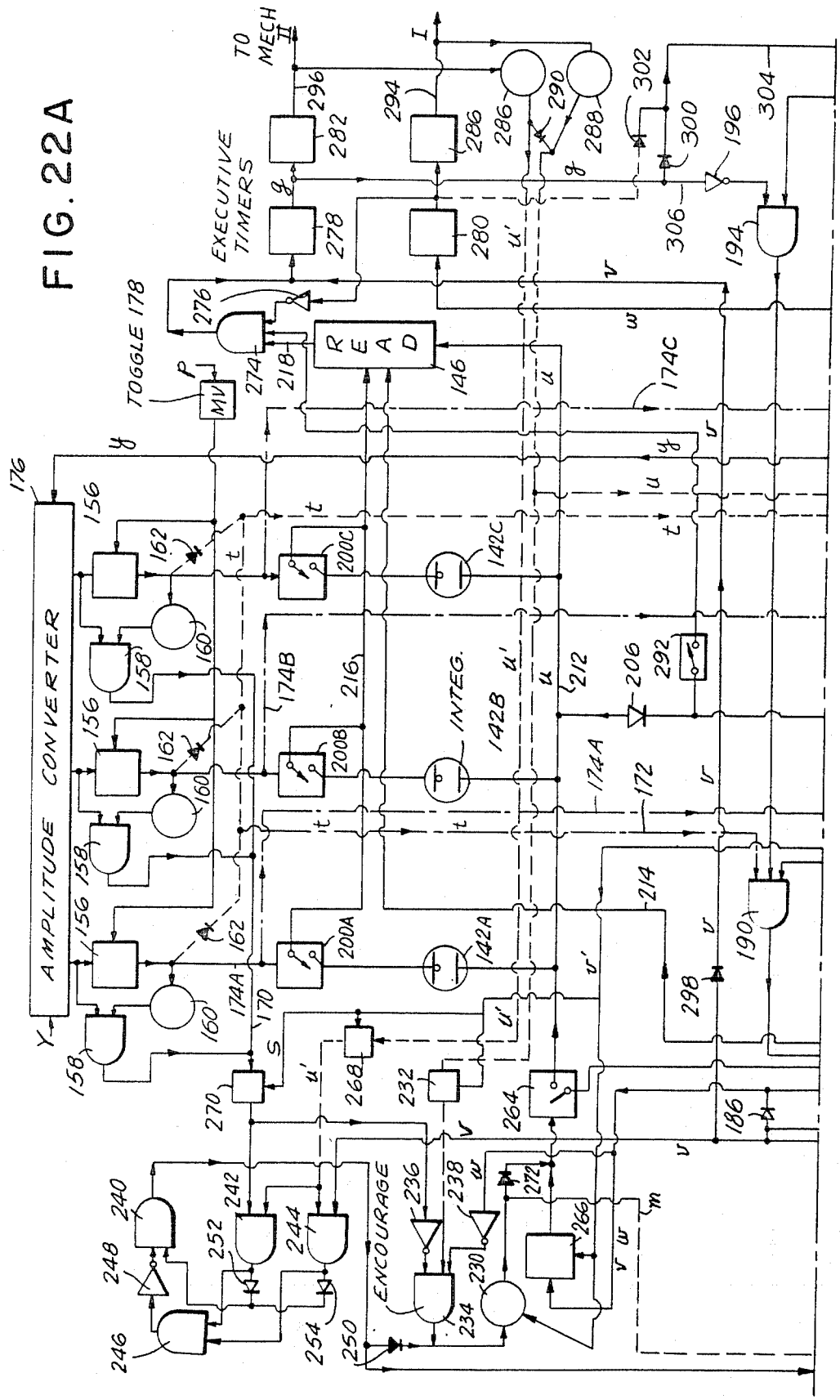

With reference now to FIG. 2, (and also with reference to FIGS. 22A–22B which will also be useful for viewing the interconnections of elements in many of the suceeding figures) there is shown a more detailed diagram of the signal processor 132 of FIG. 1. The precursor signal, Y, is applied to an amplitude converter 176 comprising the aforementioned window comparators 154 which quantize the analog precursor signal to specific ranges of amplitude. The comparator 154 having the specific amplitude range, corresponding to the amplitude of the precursor signal, provides an output logic 1 signal to the corresponding register 156 and AND gate 158. Since the output signal of the comparators 154, in this embodiment of the invention, are one-bit signals, each register 156 may be fabricated as a single flip-flop. The registers 156 are strobed by a pulse from a multivibrator 178 to store the signals from the converter 176. The multivibrator 178 is strobed by a timing signal, p, as will be further described subsequently. The multivibrator 178 is constructed in the form of a toggle flip flop wherein the logic state of the output signal is altered for each occurrence of the input timing signal p. The strobing by the multivibrator 178 resets each of the registers 156 so as to clear them of the data stored therein, upon alternate occurrences of the signal p, whereupon further data is entered into the registers 156 upon the occurrence of the y signal. The y signal serves as a gate signal for the comparators 154 and is provided by timing circuitry as will be described subsequently. The gate signal, y, may be applied to a comparator 154 by any one of well known circuits (not shown) such as by use of an AND gate to the output terminal of a comparator 154.

Figure 3:
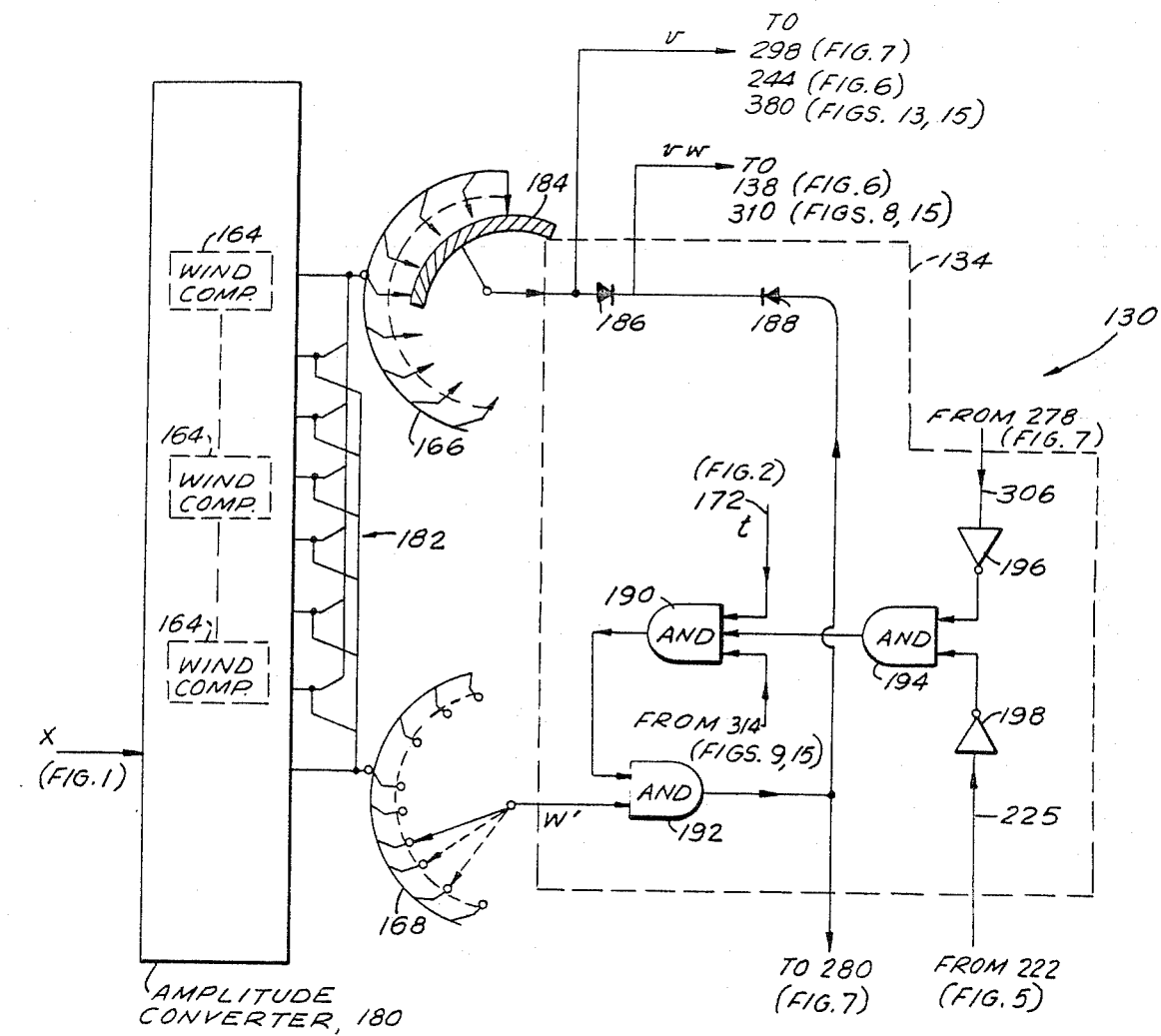
FIG. 3 is a schematic diagram of a signal processor of FIG. 1 for processing a condition signal.

Referring now to FIG. 3, there is shown a more detailed diagram of the signal processor 130, previously shown in FIG. 1. The input condition signal, X, is first processed by an amplitude converter 180 comprising the foregoing set of window comparators 164. The circuitry and operation of the comparators 164 follow that described above for the comparators 154. Thus, the continuously variable analog signal X is converted to a discrete set of output signals on lines 182 which fan into the terminals of the switches 166 and 168. The lines 182 are coupled to respective ones of the comparators 164, one of the lines 182 attaining a logic 1 signal when the amplitude of the X signal falls within the range of values of the corresponding window comparators 164. The signals of the other ones on the lines 182 would, accordingly, be at logic 0. The switch 166 includes a sliding contact 184 which simultaneously contacts a plurality of the fixed contacts to accomplish the foregoing connection, described in reference to FIG. 1, wherein the output signals of all of the comparators 164 which fall within the danger zone of blood pressure in the patient 102 are coupled to the output terminal of the switch 166. Also, as was noted previously with reference to FIG. 1, in switch 168, connection is made with only one of the window comparators 164 so that a logic 1 signal appears on the output terminal of the switch 168 only in the circumstance wherein the amplitude of the X signal falls within the relatively narrow border region immediately below the threshhold of the danger zone. When no signal appears at any of the output terminals of the comparators 164 coupled to the switches 166 and 168, the blood pressure is in the normal range of values.

The timing circuits 128 and 134 and the logic circuit 140 of FIG. 1 are interconnected and operate together to accomplish the timing and steering of the various signals to the requisite locations at the correct times. Thus, portions of timing circuit will be found in the logic circuit 140, and portions of logic, or signal steering, circuits will be found in the timing circuits 218 and 134. More specifically, with reference to FIG. 3, the input timing circuit 134 comprises two diodes 186 and 188 for signal combining and steering, three AND gates 190, 192 and 194, and two inverters 196 and 198.

It is readily seen that the input timing circuit 134 utilizes signals from various parts of the overall system 100, these signals being utilized for gating the border-region signal of the switch 168, and for providing output signals of the processor 130 from a combination of the signals of both the switches 166 and 168. The signal from the output terminal of the switch 168 is coupled via the AND gate 192 and is identified as a signal w on line w which is coupled to the output timing circuit 128 for control and execution of the first mechanism 114, the w signal also being applied to the diode 188. The signal at the output terminal of the switch 166 is identified as the v signal on line v which is applied to the output timing circuit 128 for control and execution of the second mechanism 116, and is also applied to punishment circuitry within the unit 138 as well as to other timing circuitry. By means of the diodes 186 and 188, the v signal and the w signal are applied to a common signal line, identified as the vw line for use in the operation of the positive correlation, in the encouragement circuitry of the unit 138, and in the timing circuitry. The utilization of the w, v, and vw signals will be described in further detail hereinafter. The gating signal for operation of the AND gate 192 is provided by the AND gate 190, the AND gate 190 being operated, in turn, by signals from the AND gate 194 in combination with the single-event signal, t, on line 172 (FIG. 1) and a signal from a timing unit as will be described further hereinafter. The AND gate 194 is operated by signals coupled via the inverters 196 and 198, respectively, from the output timing circuit 128 in conjunction with the operation of the second mechanism 116 and from a signal from the negative correlation of the unit 136 (FIG. 1). The coupling of the two signals via the inverters 196 and 198 establishes the situation wherein the border-zone signal is to be coupled from the switch 168 to line w. A further condition in the activation of the w signal is introduced by the single-event signal on line 172 at the AND gate 190 with timing of the activation of the w signal being provided from timing circuitry via the third input terminal of the AND gate 190. Thus, only upon the occurrence of the foregoing four conditions, is the border-zone signal coupled from the switch 168 via the gate 192 to appear at line w.

Figure 4:
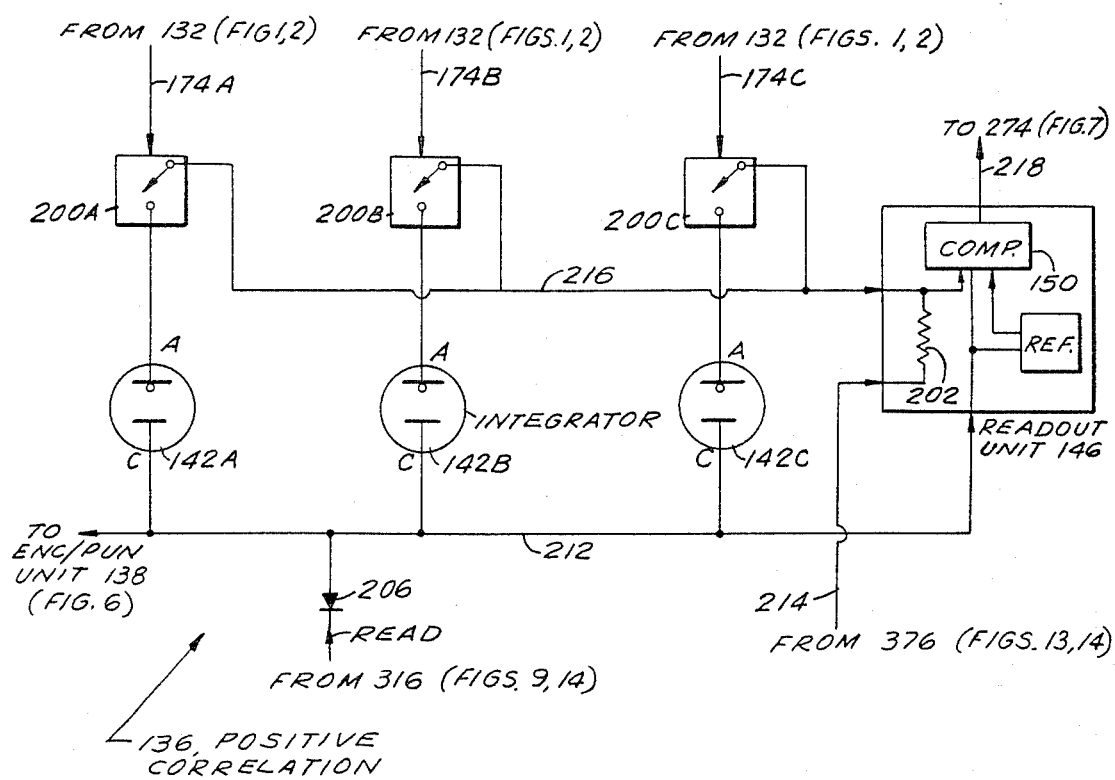
FIG. 4 is a schematic diagram of the circuitry of a set of integrators used for positive correlation in FIG. 1.

Referring now to FIG. 4, there is shown a portion of the circuitry of the correlation storage unit 136 which provides for the positive correlation. FIG. 4 shows the integrators 142 and the readout unit 146 previously described with reference to FIG. 1. In addition FIG. 4 shows switches 200, a resister 202, and a diode 206. The integrators 142 may be fabricated by means of counters (not shown) in the event that digital circuitry is to be employed in the construction of the correlation storage unit 136. However, in the preferred embodiment of the invention, the unit 136 is constructed of analog circuitry and, furthermore, is designed for the long-term storage of integrated values over relatively long periods of time, weeks and months, even in the absence of the application of electric power to the system 100. Accordingly, the integrators 142 in the preferred embodiment of the invention, are fabricated as electrochemical cells known commercially as memistors wherein the cell comprises an anode and a cathode spaced apart and immersed in a solution of an ionic salt of an electrically conductive metal, typically copper. In the presence of electric current flowing through the integrator 142, copper from the copper solution precipitates on an electrode, or alternatively is dissolved into the solution, in accordance with the direction of the current flow between the electrodes of the cell. Precipitation of the copper upon the electrode structure decreases the resistance of the cell. Reabsorption of the copper into the metallic salt solution increases the resistance of the cell of which the integrator 142 is fabricated. Thus, the resistance of the cell is dependent on the amount of precipitation of the metal. The amount of precipitation is, in turn, dependent on the integral of the current which integral is equal to the charge imparted to or removed from the cell. The resistor 202 and the readout unit 146 are serially connected with individual ones of the integrators 142. Energization of the correlation storage unit 136 is accomplished by means of voltage sources, as will be described subsequently. Such voltage sources are coupled via the resistor 202 which resistor has resistance substantially greater, for example ten to twenty or more times greater than the internal resistance of an integrator 142 whereby the current flow through an integrator 142 is substantially independent of the internal resistance of the cell of the integrator 142. Thereby, the aforementioned voltage sources in combination with the relatively large resistance of the resistor 202 function as current sources for driving predetermined amounts of current through individual ones of the integrators 142. By timing the duration of such currents, specific amounts of charge are accumulated by or dissipated in the integrators 142, depending on the sense of such current.

In reading out a signal representative of the presence or absence of a stored value in an integrator 142, the voltage drop across the integrator 142 is representative of the resistance thereof in view of the substantially fixed predetermined value of current applied to the integrator 142. The foregoing voltage is applied between the lines 212 and 214, the line 212 joining the cathode terminals (c) of the integrators 142, while the line 214 connects between the foregoing sources of voltage and the resistor 202. A line 216 joins together the anode terminals (A) of the integrators 142, the line 216 being coupled via the switches 200 to individual ones of the anode terminals. The switches 200, are in turn, operated in response to logic 1 signals applied via corresponding ones of the lines 174 A–C from the signal processor 132 as was described with reference to FIG. 1.

Measurement of voltage drop across the integrators 142 is accomplished in the readout unit 146 by means of the comparator 150 (FIG. 1), the readout unit 146 providing a logic 1 signal on line 218 when the value of the voltage drop of an integrator 142 exceeds a reference value of voltage supplied, in a well known manner, to an input terminal of the comparator 150.

Thus, in accordance with yet another feature of the invention, the value of stored data within the integrators 142 is quantized to a single bit, such that the voltage drop developed across an integrator 142 with the storage of an integrated value would be quantized to a value above or below that of the reference voltage to the comparator 150. The magnitude of the reference voltage is selected to be equal to approximately one-half of the increment in voltage drop associated with the establishment of one unit of charge within the electrochemical cell of the integrator 142.

As has been noted previously, not all of the integrators 142 are utilized simultaneously but, rather, only one integrator 143 is to be implemented for the writing, reading or erasing of data corresponding to the amplitude of the precursor signal. The selection of a specific one of the integrators 142 is governed by the signal of a line 174, that signal activating the corresponding one of the switches 200 for the selection of the corresponding one of the integrators 142. Thereby, upon activation of a specific one of the integrators 142 via the corresponding switch 200, and by the establishment of a reading voltage betweeh the lines 212 and 214, the comparator 150 of the readout unit 146 is responsive to the voltage drop between the anode and the cathode terminals of the selected integrator 142. The resultant reading of the stored data, to within one bit is provided by the signal on line 218 coupled from the readout unit 146 to the output timing circuit 128 (FIG. 1). The voltage for the reading operation is applied via the diode 206, while the voltages for the writing and erasing operations are provided by the encouragement/punishment unit 138 coupled to line 212 as will be described subsequently. The erasing and reading voltages have polarities of the opposite sense to the polarity of the writing voltage, the diode 206 providing for the coupling of the voltages of the opposite sense. For the writing, erasing and reading functions, voltages in range of 2 to 12 volts are acceptable for proper operation of the memistors of the integrators 142.

As has been noted with respect to the line 152 (FIG. 1) coupling the readout unit 142 to the correlation storage unit 136, the reading operation provides for a reduction in the magnitude of the values stored in the integrator 142 for which a reading is being provided. The line 152 of FIG. 1 represents the function of decrementing the magnitude of the integrated signal, the actual operation of the decrementing being accomplished as follows: As has just been described, the sense of the reading voltage is opposite that of the writing voltage and equal to the sense of the erasing voltage. Thereby, during the reading operation, current passes through the integrator 142 in the direction opposite to that of the writing operation. Accordingly, wherein the writing operation results in a precipitation of further metal upon an electrode of the integrator 142, the opposed sense of the reading current results in a dissolving of a portion of the precipitated metal, thereby reducing or decrementing the magnitude of the stored data.

Figure 5:
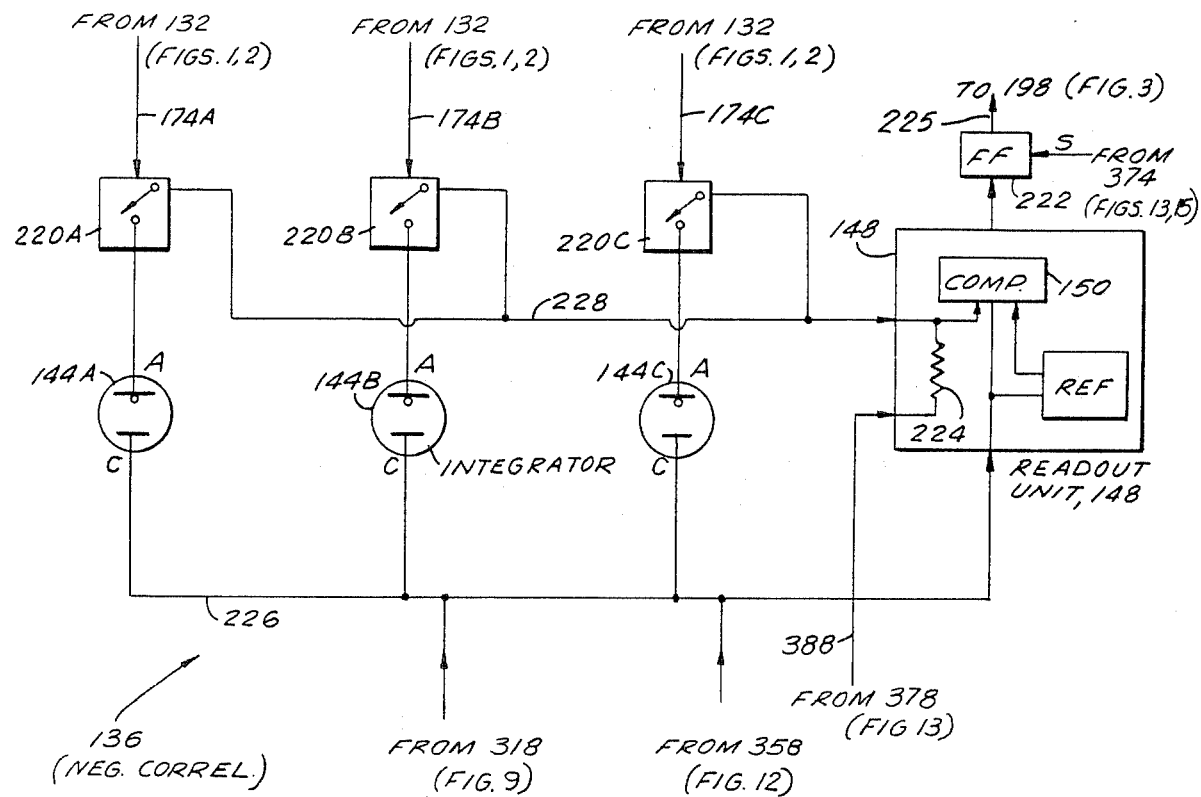
FIG. 5 is a schematic diagram of the circuitry of a set of integrators used for negative correlation in FIG. 1.

Referring now to FIG. 5, there is shown a detailed schematic drawing of the portion of the circuitry of the correlation storage unit 136 (FIG. 1) for the negative correlation function. The circuitry includes the integrators 144 and the readout unit 148 previously described in FIG. 1, the circuitry further comprising a set of switches 220, a flip-flop 222 and a resistor 224. The readout unit 148 includes the comparator 150, also described previously with reference to FIG. 1, the readout unit 148 functioning in the same manner as was described above for the readout unit 146. The integrators 144 are of the same form as and function as do the integrators 142 of FIGS. 1 and 4. The switches 220 are of the same form and function as to the switches 200 of FIG. 4. Also, the resistor 224 has a resistance much larger than the resistance of an integrator 144 and functions in the manner described above for the resistor 202 (FIG. 4) for converting the operation of the voltage sources to that of a current source for driving current through the integrators 144 in the writing and reading operations. The flip-flop 222 is of the set-reset form, and is set upon the appearance of a logic 1 signal from the readout unit 148. The flip-flop 222 is reset by the s signal provided by timing circuitry as will be described subsequently. The output terminal of the flip-flop 222 is coupled with line 225 to an input terminal of the inverter 198 of FIG. 3.

The operation of the positive and negative sections of the correlation storage unit 136, FIGS. 4 and 5, are the same. The cathodes (C) of the integrators 144 are coupled together to the readout unit 148 by a line 226, and the anodes (A) of the integrators 144 are coupled together via the switches 220 and a line 228 to a terminal of the readout unit 148. In response to the flow of current via the lines 226 and 228 and through a selected one of the integrators 144, a voltage drop appears between the lines 226 and 228, which voltage drop is applied to the comparator 150. The foregoing current is coupled via the resistor 224, the sense of the current determining whether metal is precipitated upon an electrode of an integrator 144 or re-absorbed therefrom into the solution within the electromechanical cell of the integrator 144 as was the case with the integrators 142 of FIG. 4. During readout of the stored data of the integrators 144, there is a reduction or decriment in the amount of stored data provided by the readout current, as is the case for the circuitry of FIG. 4. With respect to the circuitry of FIG. 5, there are two voltage sources, as will be described hereinafter, which are coupled via switches to the line 226 to provide for the writing and reading functions. With respect to the circuitry of FIG. 4, the circuitry provides for the coupling of two voltage sources for writing and reading and, in addition, provides for the coupling of a third source of voltage for the aforementioned erasing function.

Figure 6:
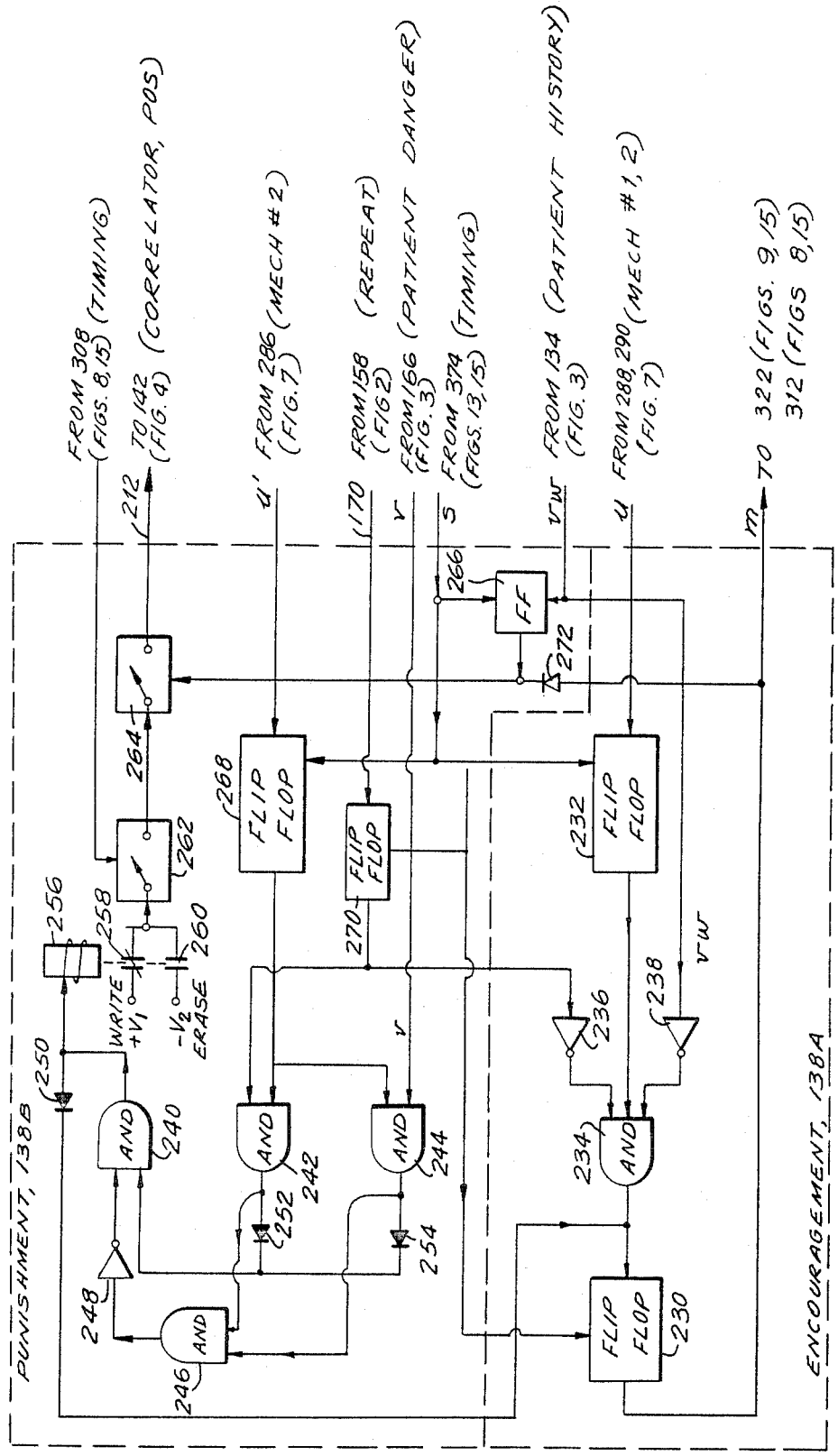
FIG. 6 is a schematic diagram of an encouragement/punishment unit of FIG. 1.

Referring now to FIG. 6, the encouragement/punishment unit 138 comprises two sections, an encouragement section 138A and a punishment section 138B which are coupled together as shown in the schematic drawing of FIG. 6. The encouragement section 138A comprises two flip-flops 230 and 232, an AND gate 234 and two inverters 236 and 238. The punishment section 138B comprises four AND gates 240, 242, 244, and 246, an inverter 248, three diodes 250, 252, and 254, a relay 256 having a normally-closed contact 258 and a normally-open contact 260, two switches 262 and 264, three flip-flops 266, 268 and 270, and a diode 272 connecting between the sections 138A and 138B.

In the encouragement section 138A, the two flip flops 230 and 232 are reset by the s signal provided by the timing circuitry as will be described subsequently. In particular, it is noted at this time that the s signal appears cyclically with each cycle of the operation of the system 100, the s signal occurring immediately upon receipt of the v signal (FIG. 3) for blood pressure of the patient 102 (FIG. 1) in the danger zone. The flip-flop 232 is set by the u signal from the output timing circuit 128 (FIG. 1) which signal is produced upon activation of either one of the mechanisms 114 and 116. The AND gate 234 is responsive to the output signal of the flip-flop 232 and is also responsive to the vw signal (FIG. 3) coupled via the inverter 238, and the repeat signal on line 170 (FIG. 2) applied by the flip-flop 270 and the inverter 236.

The flip-flop 270 is reset by the s signal and is set by the repeat signal on line 170. In accordance with the foregoing dependency on the repeat signal, the output signal of the flip-flop 270 is coupled via the inverter 236 to an input terminal of the AND gate 234. A logic 1 signal at the output terminal of the AND gate 234 sets the flip-flop 230 to provide a logic 1 signal, identified by the letter m. The m signal is coupled via the diode 272 to operate the switch 264 in the punishment section 138B, and is also applied to timing circuits as will be described subsequently.

In the punishment section 138B, the flip-flops 266 and 268 are reset by the s signal, the flip-flop 266 being set by the aforementioned vw signal. The flip-flop 268 is set by a signal u provided by the output timing circuit 128 (FIG. 1) upon the activation of the second mechanism 116. The switch 264 is activated, as noted above, by the m signal via the diode 272, and is also activated, alternatively, by the logic 1 signal of the flip-flop 266. The switch 264 is serially connected with the switch 262, the latter being activated by a signal from the timing circuitry as will be described subsequently. The switch 262 is coupled to the contacts 258 and 260 for providing either the voltage V1 or V2 via the switch 264 to the line 212 of the positive portion of the correlation storage unit 136 (FIG. 4). The selection of the voltage V1, which is of a positive polarity, or the voltage V2, which is of a negative polarity, is accomplished by activation of the relay 256. Thereby, the relay 256 provides writing and erasing voltages for the integrators 142 (FIG. 4) in accordance with signals developed by the timing circuitry, to be described subsequently, and in accordance with signals developed by the encouragement section 138A and the punishment section 138B. Thereby, the operation of the positive section of the correlation storage unit 136 is coordinated with other operations of the system 100.

The flip flops 268, 270 and 232 serve as buffer storage units for storing their respective input signals until such time as they are reset by the s signal. The u' signal of the flip-flop 268 is applied to input terminals of both AND gates 242 and 244. The repeat signal is applied via the flip-flop 270 to the AND gate 242, as well as to the inverter 236, while the v signal designating the danger zone is applied from the signal processor 130 (FIGS. 1 and 3) to an input terminal of the AND gate 244. Output signals of the AND gate 242 and 244 are coupled by diodes 252 and 254 to an input terminal of the AND gate 240. The output terminal of the AND gates 242 and 244 are also coupled to respective input terminals of the AND gate 246. The output terminal of the AND gate 246 is coupled via the inverter 248 to an input terminal of the AND gate 240. The output terminal of the AND gate 240 is coupled to the coil of the relay 256 for activating the relay 256, the output terminal of the AND gate 240 also being coupled via the diode 250 to the flip flop 230 in the encouragement section 138A. The diodes 250, 252, and 254 thus serve as steering diodes whereby a plurality of signals can be coupled together by a common terminal.

In operation, the interconnection of the components of the circuitry of FIG. 6 provides for a logic arrangement wherein the functions of punishment and encouragement are attained in response to the condition of the patient 102 (FIG. 1) and in response to previous attempts to correct his condition by means of the first and second mechanisms 114 and 116 (FIG. 1). For example, in the situation wherein the second mechanism has been employed, yet there has been no change in the value of the precursor signal, Y, in view of the repeat signal on line 170, and AND gate 242 activates the AND gate 240 to energize the relay 256 to "punish" the correlation storage unit 136 (FIG. 1). The punishment is applied by the coupling of the magnitude voltage V2 through the switches 262 and 264 to the integrators 142 (FIGS. 1 and 4). However, in the event that the blood pressure of the patient remains in the danger zone in spite of the implementation of a dosage of medicine by the second mechanism 116, as designated by the presence of the v signal from the switch 166 in the processor 130 (FIGS. 1 and 3), then the AND gates 242 and 244 together activate the AND gate 246 to de-activate the AND gate 240 for de-energization of the relay 256. Thereby, the negative voltage V2 is not coupled to the switch 262. In addition, the output signal of the AND gate 240 which is coupled via the diode 250 to the flip-flop 230 activates the m signal concurrently with the energization of the relay 256, the m signal having a state of logic 0 in the foregoing situation wherein the relay 256 is de-energized. Thus, the switch 264, controlled by the m signal, would remain open so that no write or erase signal voltage would be applied to the correlation storage unit 136. (It is noted that flip-flop 230 and its output m signal can be separately activated by the AND gate 234 during some other patient situation different from the example presently being described.)

By way of further example in operation of the encouragement/punishment unit 138, the AND gate 234 is activated to provide for a further application of the writing voltage V1 to the line 212 of the positive-correlation integrators 142 for implementing the stored data therein. The activation of the AND gate 234 occurs in the situation wherein there has been no repetition of the value of the precursor signal, Y, (line 170 in FIGS. 1 and 2) this being a situation wherein the pulse rate of the patient 102 is responding to the application of the medication by the mechanisms 114 and 116. The foregoing relationship between the lack of repetition in the precursor signal is attained by virtue of the inverter 236 coupled between the flip-flop 270 and an input terminal of the AND gate 234. A further requirement for the implementation of the encouragement is imparted by the inverter 238 which mandates that there be no unfavorable history in the response of the patient to the medication. This may be further understood by review of the vw signal described previously with reference to FIG. 3. Thus, the vw signal occurs in the absence of a blood pressure in the danger zone, in the absence of the utilization of the second mechanism 116, and in the absence of the storage of a negative value of correlation in the integrator 144 of the correlation storage unit 136. When the foregoing conditions are present, the encouragement is implemented upon the occurrence of the u signal from the output timing unit 128 indicating the activation of the first mechanism 114. All of the input signals to the AND gate 234 are then at a logic 1 level for setting the flip-flop 230 to provide the m signal with the resultant closing of the switch 264 for coupling the writing voltage V1 to the integrators 142.

The switch 264 can also be closed directly in response to the vw signal via the setting of the flip-flop 266. Such closure of the switch 264 enables the connection of the writing voltage V1 for incrementing the value of the signal stored in any one of the integrators 142 to record the occurrence of a positive correlation between the concurrent occurrence of the X and Y (condition and precursor) signals of FIG. 1.

Figure 7:
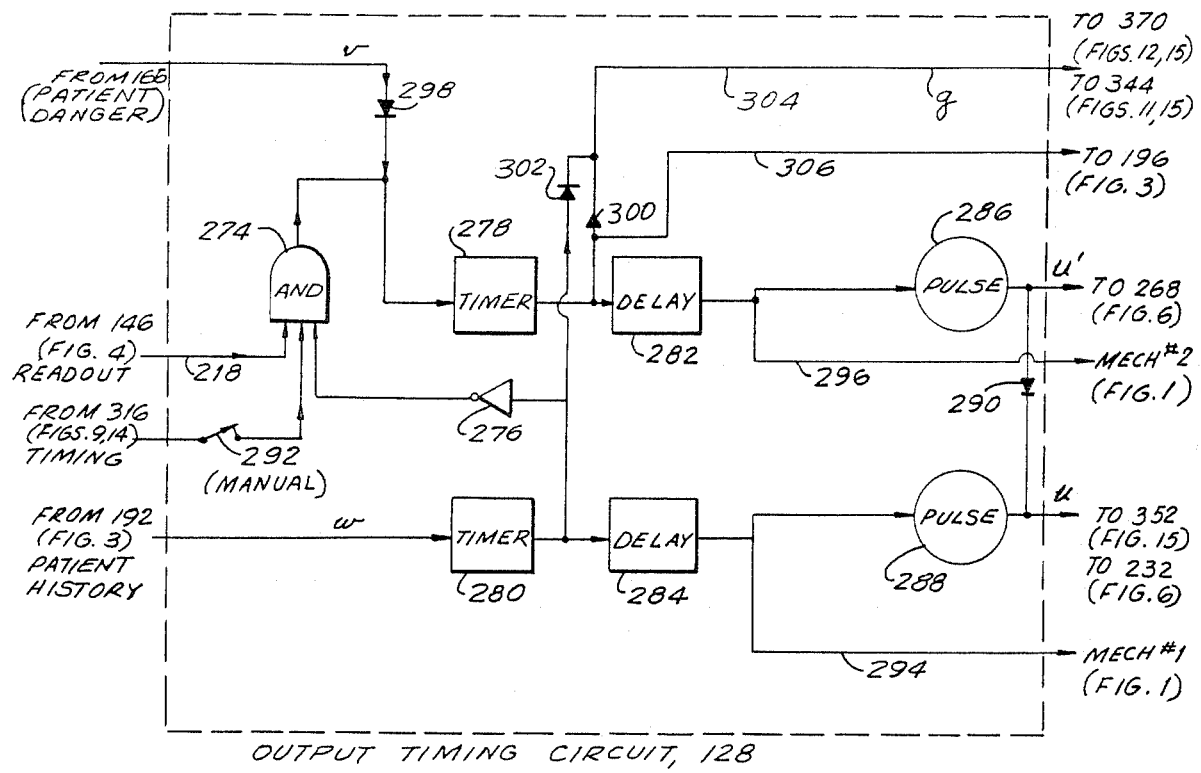
FIG. 7 is a schematic diagram of an output timing circuit of FIG. 1.

Referring now to FIG. 7, the output timing circuit 128 comprises an AND gate 274, an inverter 276, timers 278 and 280, delay units 282 and 284, pulse generators 286 and 288, a diode 290 and a manually operated switch 292. The output timing circuit 128 provides a signal along line 294 to activate the valve 124 (FIG. 1) of the first mechanism 114. The circuit 128 provides a signal along line 296 to operate the valve 124 of the second mechanism 116.

With reference also to FIG. 3, the signal v is applied via diode 298 to activate the timer 278, the signal v designating a blood pressure of the patient 102 which is dangerously high. The signal w is coupled from the AND gate 192 (FIG. 3) to activate the timer 280 (FIG. 7), the signal w arising from the borderline region of the patient's blood pressure and being coupled by the gate 192 under the set of circumstances previously described with respect to FIG. 3. The timer 280 is utilized for activating the first mechanism 114, the timer 280 setting the duration of the interval of time during which the valve 124 of the first mechanism is to be open for allowing medication to flow along the tube 126 (FIG. 1). Similarly, the timer 278 is utilized for setting the duration of time during which the valve 124 of the second mechanism 116 is to be open for allowing the passage of medication via the tube 126. The delay units 282 and 284 by which the signals of the timers, respectively, 278 and 280 are coupled to the lines 296 and 294, provide for delays between the generation of the respective signals of the timers 278 and 280 and the times of activation of the first and second mechanisms. These delays permit a physician in charge of the patient 102 (FIG. 1) to override the system 100 by deactivating the first and second mechanisms 114 and 116 (as by electrical switches, not shown, on these units) in the event that the physician so desires to insure safety of the patient.

Output signals of the timers 278 and 280 are coupled via diodes 300 and 302 to appear on line 304 by which the signals, identified by the letter g, are coupled to timing circuitry as will be described subsequently. In addition, the output signal of the timer 278 is coupled via line 306 to the inverter 196 in FIG. 3. The second mechanism 116 can also be activated through the coupling of the AND gate 274 to the timer 278, the output signal of the gate 274 activating the timer 278. A logic 1 signal appears at the output terminal of the AND gate 274 in response to logic 1 signals at the three input terminals, this including the presence of a logic 1 signal on line 218 from the readout unit 146 of the positive correlation (FIGS. 1 and 3). However, activation of the second mechanism via the signal on line 218 from the readout unit 146 does not occur in the event that the timer 280 has been activated in view of the connection of the output terminal the timer 280 via the inverter 276 to an input terminal of the AND gate 274. Upon activation of the timer 280, the output signal of the inverter 276 goes low deactivating the AND gate 274. In addition, no activation of the second mechanism 116 occurs in response to the signal on line 218 if the manually operated switch 292 is open, since such opening of the switch 292 allows the corresponding input terminal of the AND gate 274 to drop to the logic 0 state, thereby de-activating the gate 274. The pulse generator 286 is triggered by the leading edge of the output signal of the delay unit 282 to provide a pulse signal, the u' signal for use by the encouragement/punishment unit 138 (FIG. 6). Similarly, the pulse generator 288 is triggered by the leading edge of the output signal of the delay unit 284 to provide a pulse signal, the diode 290 coupling the pulse signal of the generator 286 to the output terminal of the generator 288 to provide the foregoing u signal which may comprise either of the pulses of the generator 286 and 288 for use by the encouragement/punishment unit 138 (FIG. 6).

The FIGS. 8–13 portray the timing diagrams as well as the voltage sources and switching circuits therefor to which reference has been made in the foregoing description of the system 100 of FIG. 1. Each of the FIGS. 8–13 include a timer and circuitry for activating the timer. In addition, some of the circuits include switches, activated by the timers, for applying the requisite voltages for the functions of writing, reading and erasing of data stored in the integrators 142 and 144 of FIG. 1.

Figure 8:
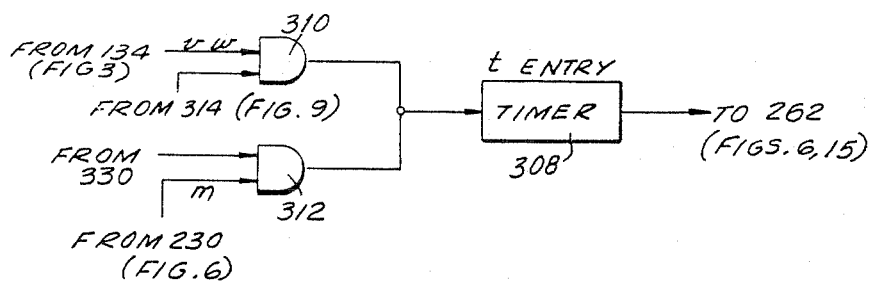
FIGS. 8, 9, 10, 11, 12 and 13 show schematic diagrams of various parts of the timing circuitry of the system of FIG. 1.

With reference now to FIG. 8, the schematic drawing shows a timer 308 providing an output signal which controls the switch 262 of FIG. 6. Two AND gates 310 and 312 have output terminals which are joined together at an input trigger terminal of the timer 308. The AND gate 310 receives the vw signal at one of its input terminals from the signal processor of FIG. 3. The m signal from the flip-flop 230 of FIG. 6 is applied to input terminal of the AND gate 312. The remaining input terminals of the AND gate 310 and 312 receive signals from timing circuits as will be described subsequently. Thereby, upon the activation of the AND gates 310 and 312 by their respective timing signals, the timer 308 can be triggered by either the vw signal through gate 310 or by the m signal through gate 312. The timing operation of the timer 308 will be further described with reference to other timing operations of the system 100 in the ensuing description.

Figures 9, 10, 11:
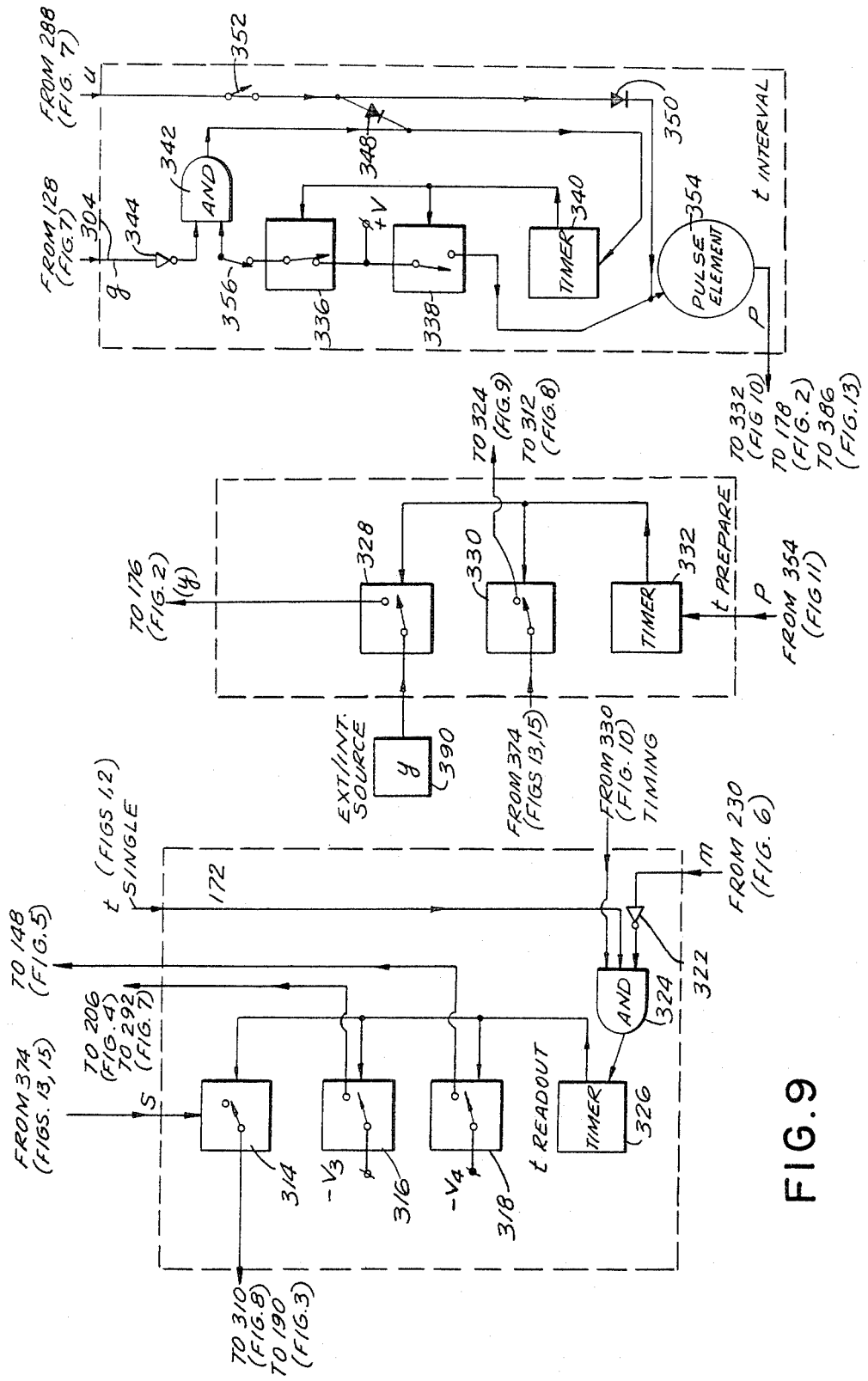

With reference to the timing circuit of FIG. 9, the circuit comprises three switches 314, 316 and 318, inverter 322, an AND gate 324 and a timer 326. The switches 316 and 318 are in the normally-open configuration, the switches being activated by an output signal from the timer 326. The switch 314 is in the normally-closed configuration and is activated by the output signal of the timer 326 applied to the control terminal of the switch 314. Thereby, upon application of the output signal of the timer 326 to the switches 314, 316 and 318, the switches 316 and 318 become closed, while the switch 314 becomes opened.

In operation, the timer 326 is triggered by the output signal of the AND gate 324, the AND gate 324 being responsive to three input signals. One input signal to the gate 324 is applied from timing circuitry to be described subsequently. A second input signal to the gate 324 is the single-event signal, t, on line 172 provided by the signal processor 132 of FIG. 1. The third input signal to the gate 324 is the m signal provided by the encouragement/punishment unit 138 (FIG. 6), which signal is coupled via the inverter 322 to the gate 324. In view of the foregoing connections of signals to the input terminals of the AND gate 324, triggering of the timer 326 can occur in the presence of the single-event signal on line 172, but is inhibited by the presence of the m signal due to the presence of the inverter 322 which converts the logic 1 state of the m signal to a logic 0 at the input terminal of the gate 324.

The switch 314 switches the s signal (previously referred to with reference to FIG. 6) to the AND gate 190 of FIG. 3 and to the AND gate 310 of FIG. 8. The switch 316 switches the voltage V3 to the readout unit 146 (FIG. 4) and to the AND gate 274 (FIG. 7). The switch 318 switches the voltage V4 to the readout unit 148 (FIG. 5).

Referring now to FIG. 10, the circuit comprises switches 328 and 330 and a timer 332. The switch 328 is normally-open and is activated by a signal from the timer 332. The switch 330 is normally closed and is activated by the foregoing timer signal. Thereby, upon energization of the timer signal, the switch 328 is closed and the switch 330 is opened. The timer 332 is triggered by a pulse signal p from timing circuitry to be described subsequently. The switch 328 switches the y signal for the converter 176 (FIGS. 1 and 2). The switch 330 switches the aforementioned s signal to the AND gate 324 of FIG. 9.

Referring now to FIG. 11, the circuit comprises switches 336 and 338, a timer 340, an AND gate 342, digital inverter 344, diodes 348 and 350, a switch 352 and a pulse generator 354. The switch 336 is normally closed and is activated by an output signal of the timer 340, which signal is applied to the switch 336. The switch 338 is normally open and is operated directly by the output signal of the timer 340. Thereby, upon energization of the output signal of the timer 340, the switch 336 is opened and the switch 338 is closed. The output signal of the AND gate 342 strobes the timer 340. One input terminal of the gate 342 receives an output signal, g, of the timing circuit 128 (FIG. 7) via line 304 and the inverter 344. A source of voltage V, corresponding to a logic 1 state, is coupled via switches 336 and 356 to the second input terminal of the gate 342. Thereby, upon closure of the switches 336 and 356, and upon the absence of the output signals of the timers 278 and 280 of FIG. 7, the output terminal of the gate 342 exhibits a logic 1 signal which strobes the timer 340. Closure of the switch 338 applies the logic 1 voltage, V, to the pulse generator 354, thereby activating the generator 354 to produce a pulse signal at its output terminal. Alternatively, the pulse generator 354 is activated by the u signal of the timing circuit 128 (FIG. 7) coupled via the switch 352 and the diode 350. The foregoing u signal is also coupled via the switch 352 and the diode 348 to serve as an alternative source of strobe for the timer 340. The pulse signal produced by the generator 354 is applied to the multivibrator 178 (FIG. 2) and to the timer 332 (FIG. 10).

Figure 12:
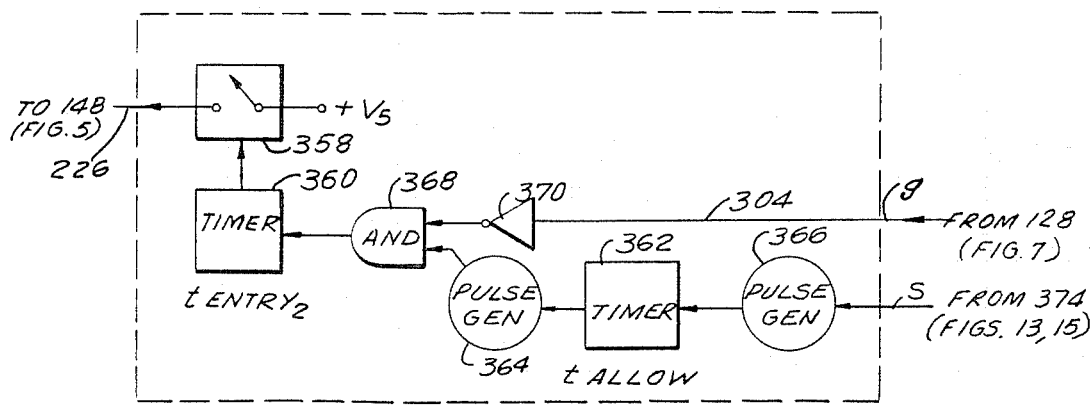

Referring now to FIG. 12, the circuit comprises a switch 358, timers 360 and 362, pulse generators 364 and 366, an AND gate 368, and a digital inverter 370. The signal on line 304 from the output timing circuit 128 (FIG. 7) is applied via the inverter 370 to one input terminal of the AND gate 368. The pulse generator 366 provides a pulse signal at its output terminal after being reset by the aforementioned s signal, the output pulse signal of the generator 366 being applied to the timer 362 for triggering the timer 362. After a predesignated amount of time, as set by the timer 362, the timer 362 triggers the generator 364 to provide an output pulse to the second input terminal of the AND gate 368. Accordingly, upon the absence of the signal on line 304, and upon the presence of the pulse signal from the generator 364, both input terminals of the gate 368 receive logic 1 signals and, accordingly, the gate 368 provides a logic 1 output signal which strobes the timer 360. Thereupon, the timer 360, after a predesignated amount of time as set within the circuitry of the timer 360, provides an output signal which activates the switch 358. The foregoing activation of the switch 358 closes the contacts thereof to couple the voltage V5 to the readout unit 148 (FIGS. 1 and 5).

Figure 13:
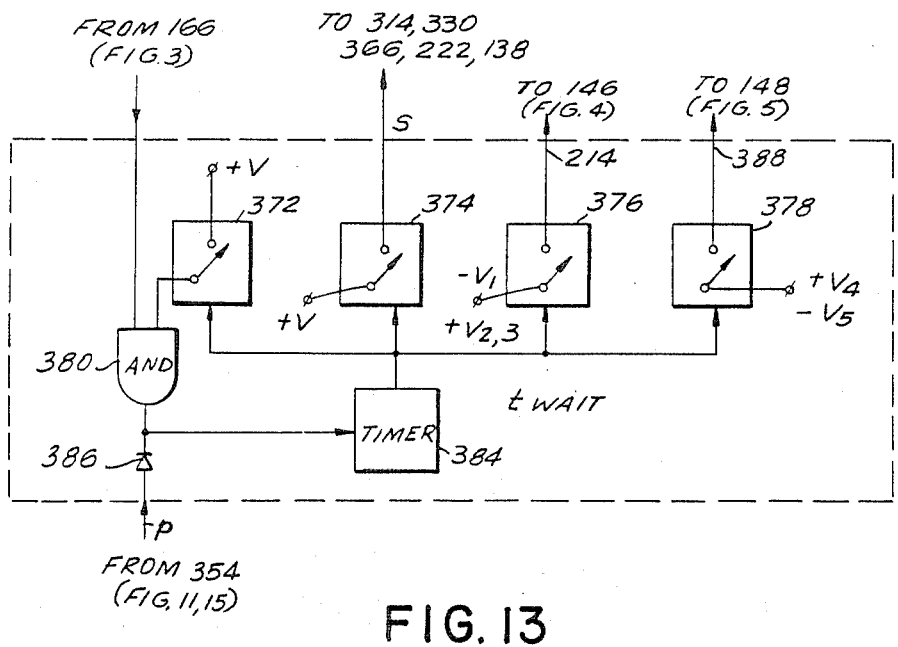

Referring now to FIG. 13, the circuit comprises four switches 372, 374, 376 and 378, an AND gate 380, a timer 384 and a diode 386. The timer 384 provides an output signal which activates the switches 374, 376 and 378, each of which are normally open and are closed upon the activation by the timer 384. The output signal of the timer 384 is also coupled to the control terminal of the switch 372, the switch 372 being normally closed, and opening upon the appearance of a logic 1 signal at the output terminal of the timer 384. The timer 384 is strobed by the output signal of the AND gate 380, and is also strobed by the p signal from the pulse generator 354 of FIG. 11. The signal p is coupled via the diode 386 to the timer 384, the diode providing for a fanning in of the p signal and the output signal of the gate 380. One input terminal of the gate 380 is activated by a logic 1 signal, namely, the v signal of the signal processor 130 (FIG. 3) while the other input terminal of the gate 380 is activated by the logic 1 voltage, V, applied to the gate 380 by the closed contacts of the switch 372. The voltage, V, is also applied to the switch 374 to provide the aforementioned s signal upon closure of the contacts of the switch 374. A terminal of the switch 376 is coupled to the junction of the voltage sources providing the voltages V1, V2 and V3, the junction of these three voltage sources being connected by the switch 376 and the line 214 to the resistor 202 of the readout unit 146 (FIG. 4) to provide the foregoing furnctions, writing, erasing and reading of the signal stored in the integrators 142. The junction of the sources providing the voltages V4 and V5 is similarly connected via the switch 378 and line 388 to the resistor 224 of the readout unit 148 (FIG. 5) to provide the functions of writing and reading of the signal stored in the integrators 144.

In the foregoing discussion of the circuits of FIGS. 8-13, all of the voltage sources have been internal sources of voltage with the exception of the voltage source 390 for the signal y applied to an input terminal of the switch 328 in FIG. 10. The voltage source 390 of FIG. 10 may be a source of voltage such as the voltage V, previously described herein, or, alternatively, may be provided by an external pulsing source which permits sampling of the Y input signal (FIGS. 1 and 2), such sampling to occur during the closure of the switch 328.

Figure 14:
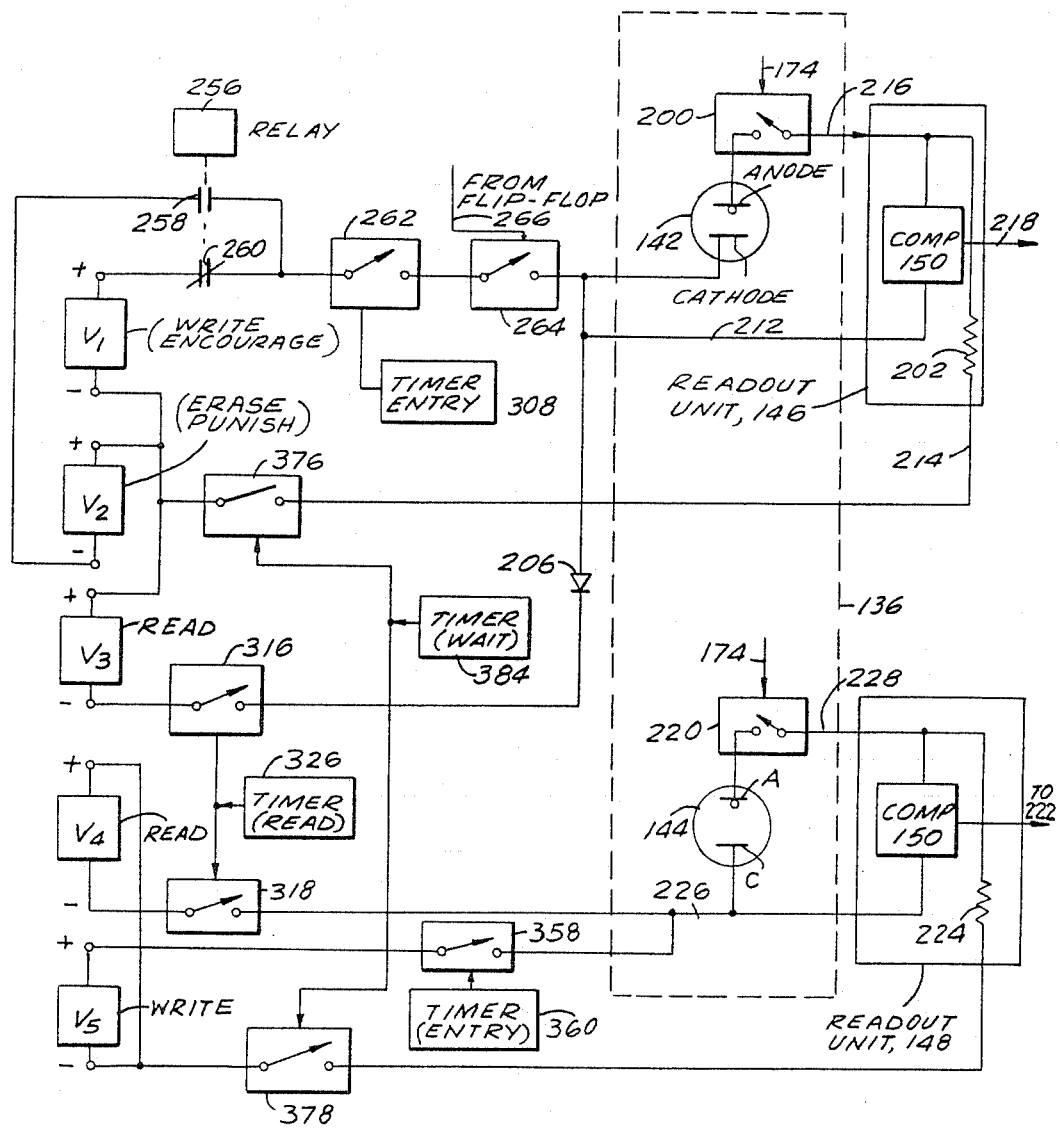
FIG. 14 shows the interconnection of elements of the timing circuitry of the preceding drawings with the integrators of FIGS. 4 and 5, and with sources of power for activating the integrators.

Referring now to FIG. 14, there is shown a portion of the correlation storage unit 136 (FIGS. 1, 4 and 5) disclosing one integrator 142 of the positive correlation and one integrator 144 of the negative correlation with their respective connections via various switches to the sources of voltage V1, V2, V3, V4 and V5. The switches and timing circuits have been described with reference to previous figures, as noted on FIG. 14 by legends appended adjacent to the various elements of the schematic drawing. FIG. 14 is useful in further explaining the operation of the system 100 (FIG. 1) to provide a further understanding of the operations of reading, writing and erasing.

For writing date into the integrator 142, the voltage is coupled via the contact 260 of the relay 256, and thence via the switches 262 and 264 to the cathode of the integrator 142. The switch 262 is controlled by the timer 308, and the switch 264 is controlled by the flip-flop 266 as has been described previously. The negative terminal of the voltage source of the voltage V1 is connected via the switch 376, under control of the timer 384, to the anode of the integrator 142 via the line 214, the resister 202 and the switch 200. Thus, during the writing operation and during the encouragement operation, current resulting from the impressment of the voltage V1 flows via the foregoing switches through the integrator 142 and through the resistor 202. The resistor 202, as has been noted previously, has a resistance much larger than that of the integrator 142 to provide, effectively, a current source arrangement with the excitation by the voltage V1. Since the value of the current flowing through the integrator 142 is thus substantially independent of the resistance of the integrator 142, the voltage drop across the integrator 142 may be regarded as being proportional to the resistance thereof. The voltage drop is sensed by the comparator 150, as has been described previously, the terminals of the comparator 150 being coupled across the series connection of the integrator 142 with the switch 200.

To accomplish the operations of erasing and punishment, the foregoing circuit is altered by the substitution of the voltage V2 in place of the voltage V1. The substitution is accomplished by the relay 256 wherein the contact 258 is closed and the contact 260 is opened, thereby connecting the negative terminal of the V2 voltage source to the switch 262 in lieu of the positive terminal of the V1 voltage source. Thereby, the resulting current flows in the reverse direction through the integrator 142 for decreasing the amount of stored data therein. Thus a negative increment appears in the resistance of the integrator 142 in lieu of the positive increment in the resistance.

To accomplish the reading operation for the integrator 142, the V3 voltage source is utilized. The negative terminal of the V3 voltage source is coupled via the switch 316 and the diode 206 to the cathode of the integrator 142. The positive terminal of the V3 voltage source is coupled via the switch 376, the line 214, the resistor 202 and the switch 200 to the anode of the integrator 142. The switch 316 is controlled by the timer 326 as has been described previously. Thereby, a current is impressed by V3 voltage in a direction through the integrator 142 which direction is the same as that utilized by the foregoing erase current. Thereby, the reading operation results in a decreasing of the amount of stored data in the integrator 142. The magnitudes of the V1 and V2 voltages are equal, while the magnitude of the V3 voltage is equal to one-half that of the V1 voltage such that two reading operations are required to reduce the magnitude of the stored data of the integrator 142 by an amount equal to the increment provided by one writing operation.

Following a similar operation, the reading of data of the integrator 144 for the negative correlation is accomplished by use of the V4 voltage. The positive terminal of the V4 voltage source is coupled via the switch 378, which is under control of the timer 384, to the resistor 224, and then via the switch 220 to the anode of the integrator 144. The negative terminal of the V4 voltage source is coupled via the switch 318, which is under control of the timer 326, via line 226 to the cathode of the integrator 144, thereby completing the circuit. In a response to the completion of the circuit, the impressed voltage V4 drives a current through the resistor 224 and the integrator 144. The resistance of the resistor 224 is substantially greater than that of the integrator 144 so that the current flow through the integrator 144 is substantially independent of the value of its resistance. Thus, the comparator 150 connected across the series combination of the integrator 144 and the switch 220 is responsive to the voltage drop and resistance of the integrator 144.

With respect to the writing operation for the integrator 144, the positive terminal of the V5 voltage source is coupled via the switch 358 and line 226 to the cathode of the integrator 144. The negative terminal of the V5 voltage source is coupled via the switch 378, which is under control of the timer 384, to the resistor 224 and then via the switch 220 to the anode of the integrator 144. Thereby, a current flows through the integrator 144 in the direction opposite to that of the current during the reading operation. The magnitude of the voltage V4 is one-half that of the voltage V5 such that two reading operations are required to reduce the stored data of the integrator 144 by an amount equal to one increment of the data prvided by a single writing operation.

Figure 15:
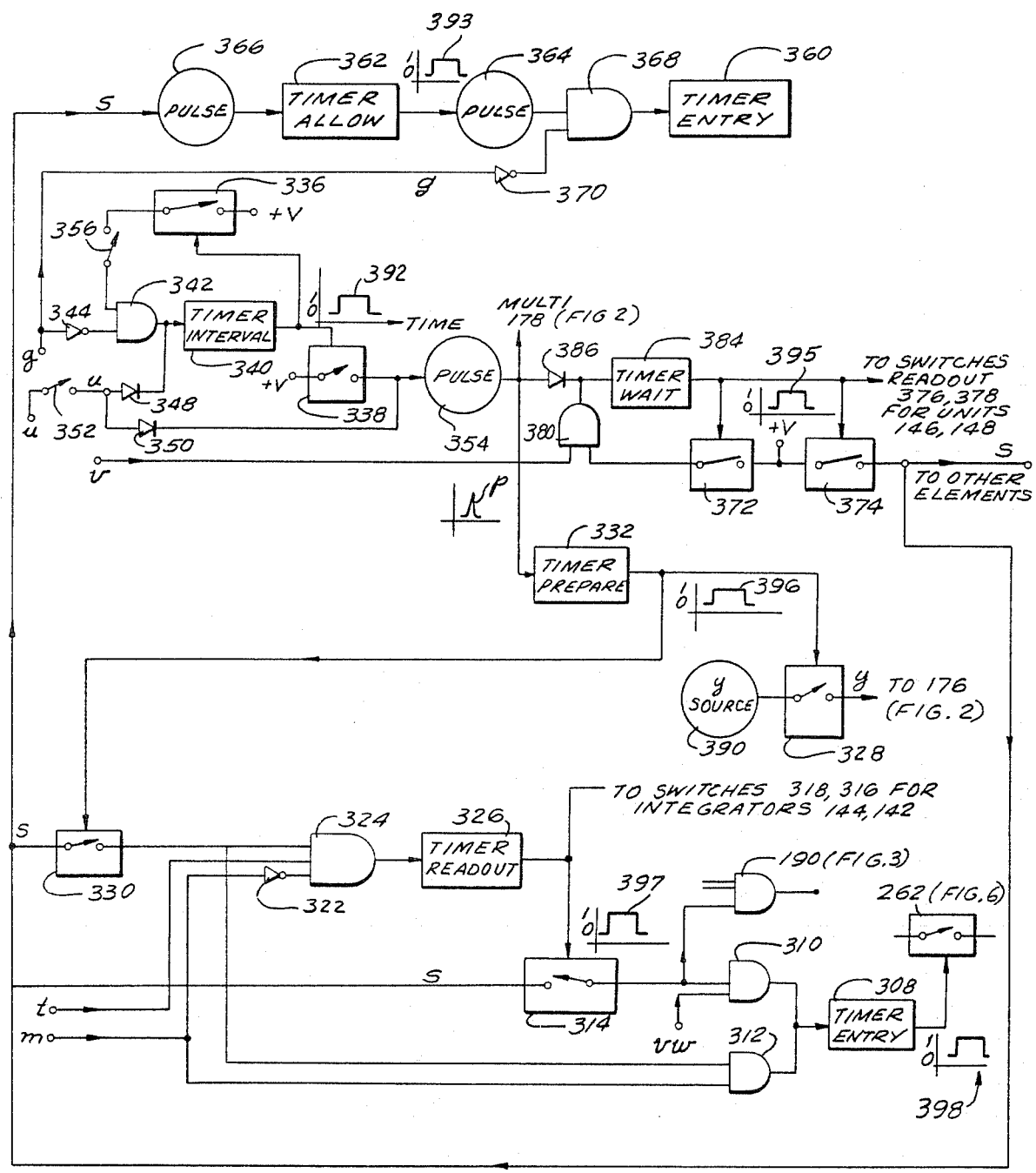
FIG. 15 shows the interconnection of various elements of the preceding timing circuits to further explain the sequential operation of the timing elements.

Referring now to FIG. 15, the schematic diagram shows the interconnection among the timers 308, 326, 332, 340, 360, 362 and 384 which have been previously described in the FIGS. 8-13. While the interconnections among the respective circuits of the foregoing timers have been disclosed in the foregoing figures, the presentation of FIG. 15 simplifies the explanation of the system operation by showing all of the foregoing timers in a single disgram while deleting some of the components of the timer circuits so as to more readily show the sequential operation of the timers. The ensuing description of the operation, therefore, summarizes and clarifies the preceding description of the operation of the timers.

The timer 340 serves as the basic timer of the interval of the repetitive operation of the system 100, the operation being periodic with a period set by the interval timer 340 unless restarted sooner by application of the u signal from the output timing circuit 128 to strobe the timer 340 to initiate a new timing interval. As shown in the graph 392 adjacent the timer 340, the output signal of the timer 340 rises from a logic 0 to a logic 1 at the beginning of the interval, and returns to the state of logic 0 at the end of the interval. The other timers 362, 360, 384, 332, 326 and 308, as shown in their respective graphs 393-398, operate in a similar fashion to the timer 340. Upon termination of the interval of the timer 340, the switch 336 closes to provide a strobe signal via the AND gate 342, in the absence of the g signal, to restart the timer 340. Since the timers 278 and 280 of the timing circuit 128 (FIG. 7) function in the same manner as does the interval timer 340, the g signal prevents restarting of the interval timer 340 during the delaying of the mechanisms 114 and 116 (FIG. 1) by the delay units 282 and 284 (FIG. 7), such restarting occuring by means of the u signal concurrently with the activation of the mechanisms 114 and 116.

The pulse generator 354 is triggered by the leading edge of the output signal of the timer 340 to produce the p signal at the beginning of the foregoing interval. The p signal strobes the wait timer 384 and the prepare timer 332 to begin their respective timing operations. The wait timer 384 may be recycled via the switch 372 and the AND gate 380 during the presence of the v signal. During the absence of the v signal, v being at a logic state of 0, the gate 380 blocks the strobe signal produced by the closure of the switch 372, so that the timer 384 can only be restarted by the strobing of the p signal.

With reference also to the timing diagrams of FIGS. 16-20, there are shown the durations, T, of the respective output signals of the interval timer 340, the wait timer 384 and the prepare timer 332, along with their respective times of occurrence. Thus, it is seen that the duration of the timing signal of the prepare timer 332 is much shorter than the duration of the timing signal of the wait timer 384.

Figure 16:
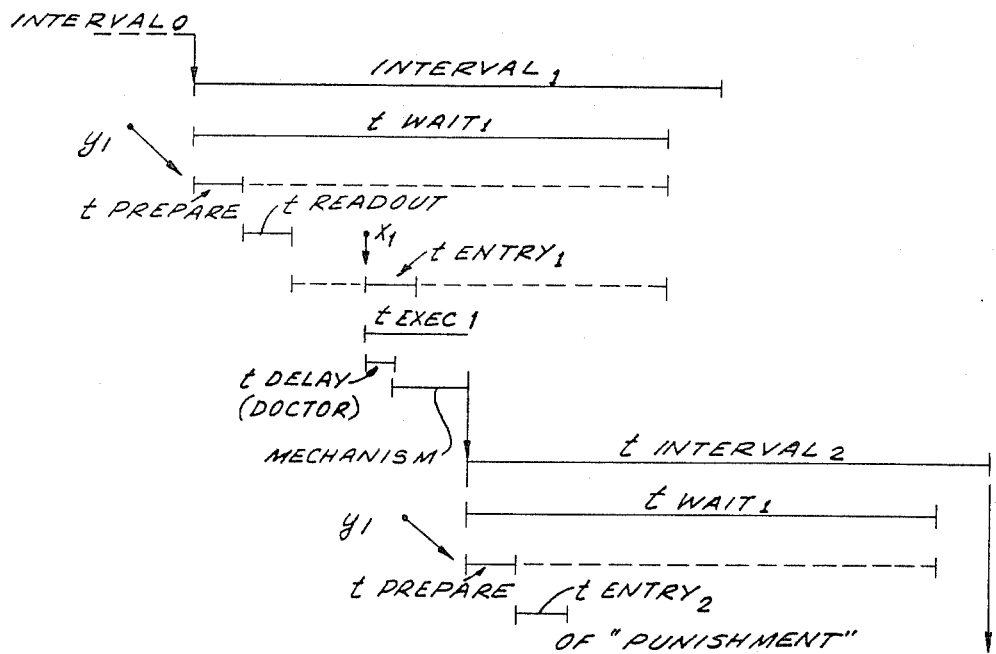
FIGS. 16, 17, 18, 19 and 20 show a sequence of timing diagrams representing a sequence of operation intervals of the system of FIG. 1.
Figure 17:
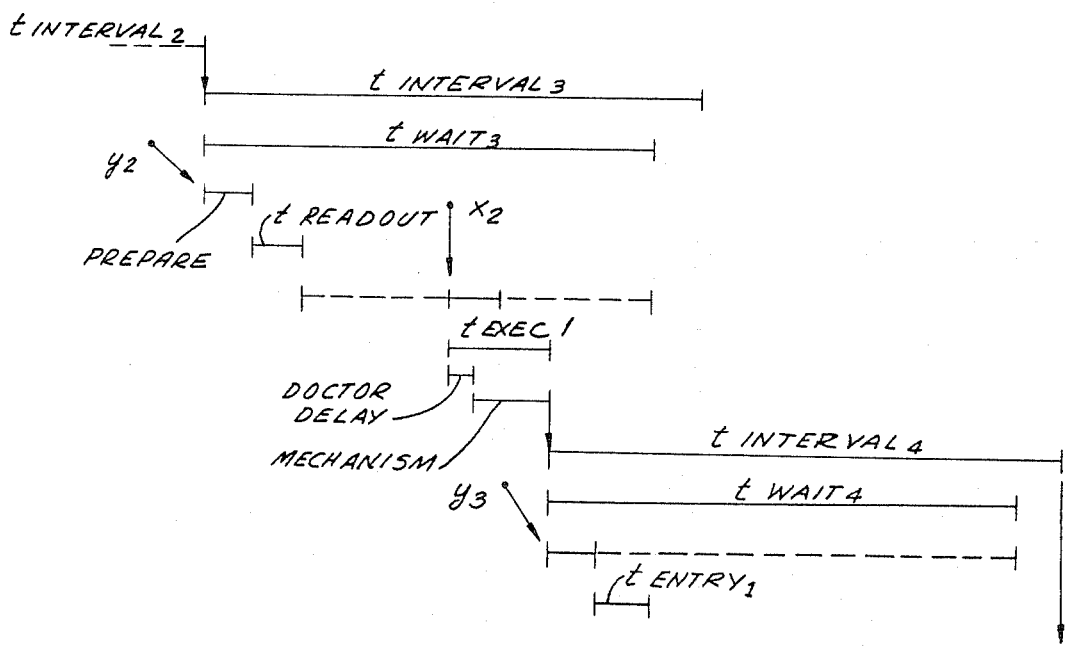
Figure 18:
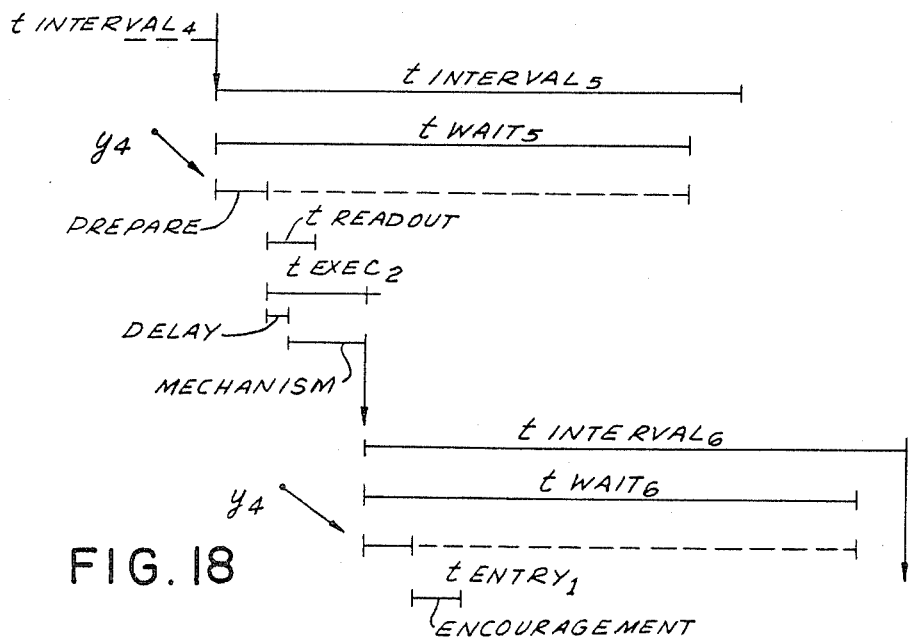
Figure 19:
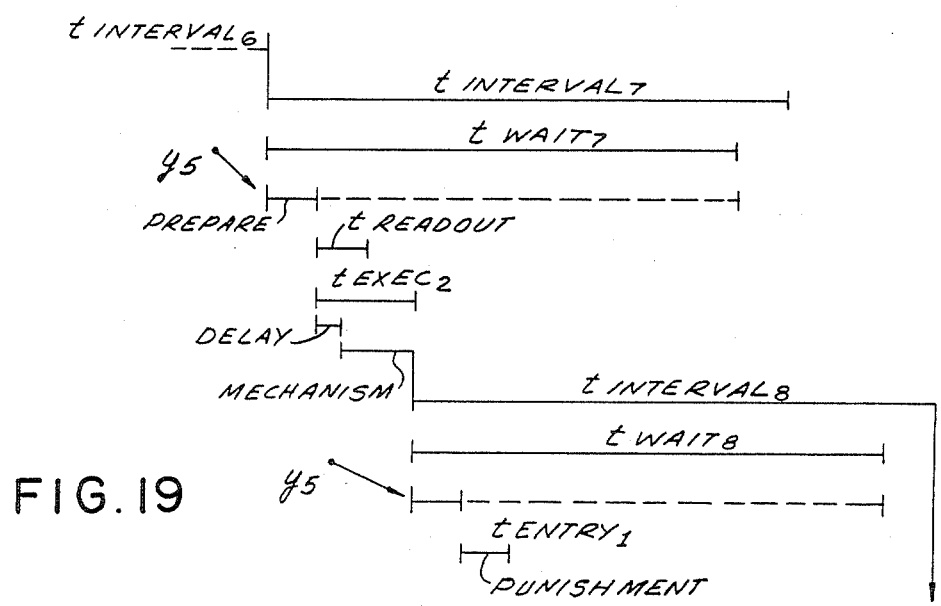
Figure 20:
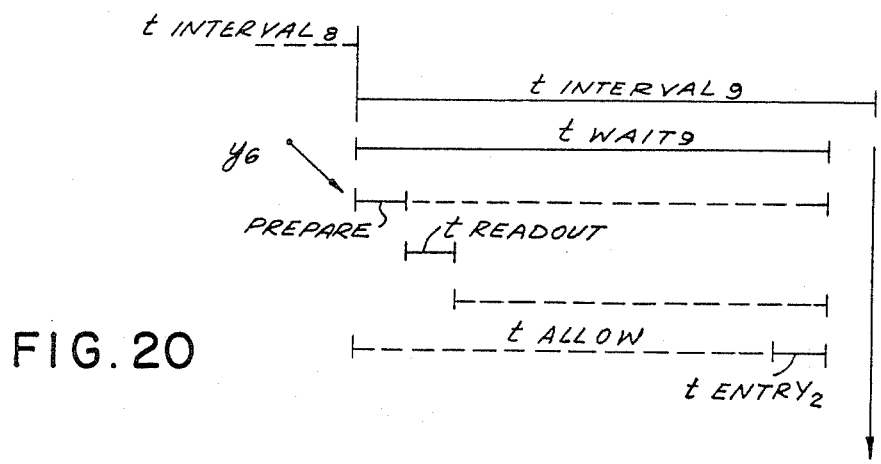

The readout timer 326 is activated by the s signal which, in turn, is produced by the closure of the switch 374 by the wait timer 384. The s signal is coupled to the readout timer 326 by the switch 330 and the AND gate 324. Since the switch 330 is opened by the prepare timer 332, the readout timer 326 is not activated until after the termination of the timing signal of the prepare timer 332. The sequential occurrence of the timing signals of the prepare timer 332 and the readout timer 326 is shown in FIG. 16.

The FIGS. 16-20 show a succession of several intervals in the operation of the system 100. The timing signals of each of the timers, namely, the wait timer 384, the prepare timer 332 and the readout timer 326, occur at the same points in time relative to each of the operation intervals set by the interval timer 340. Following the readout timing signal, there appears the signals associated with the operation of the mechanisms 114 and 116, which signals are provided by the timers 278 and 280 and the delay units 282 and 284 (FIG. 7), these signals appearing in some, but not all, of the operation intervals. For example, during activation of the second mechanism 116 by the output timing circuit 128 (FIGS. 1 and 7) in response to a signal on line 218 from the readout unit 146 (FIG. 1), such activation would occur after the timing signal of the readout timer 326. As a second example, during activation of the first mechanism 114 by the output timing circuit 128 in response to the w signal (FIGS. 3 and 7), which signal designates blood pressure in the borderline region and is coupled via the AND gate 192 under control of the AND gate 190, FIG. 15 shows the activation of the gate 190 only after the termination of the timing signal of the readout timer 326. In this respect, it is noted that the gate 190 is activated by the s signal which is produced by the wait timer 384, the s signal being coupled by the switch 314 which is driven by the readout timer 326.

The entry timer 308 (FIGS. 8, 14, 15), used for the entry of data into the integrators 142 (FIGS. 1, 4) of the positive correlation, can be activated by either the AND gate 310 or the AND gate 312. In both cases, the activation requires the presence of the s signal produced by switch 374 under control of the wait timer 384. In the case of the activation by the gate 310, the s signal does not reach the gate 310 until after closure of the switch 314 at the conclusion of the readout interval. In the case of the activation by the gate 312, the s signal does not reach the gate 312 until after closure of the switch 330 at the conclusion of the prepare interval. In the presence of the vw signal, indicating blood pressure in the danger or border regions (FIG. 3), activation of the entry timer 308 occurs via the gate 310. In the presence of the m signal, indicating either punishment or encouragement by the encouragement/punishment unit 138 (FIG. 6), activation of the entry timer 308 occurs via the gate 312. Thus, activation of the entry timer 308 can occur only subsequent to the conclusion of the prepare interval.

With respect to the entry timer 360 (FIGS. 12, 14, 15), used for the entry of data into the integrators 144 (FIGS. 1,5) of the negative correlation, the operation thereof is delayed until the latter portion of an operation interval by the allow timer 362. The timing interval of the allow timer 362 is commenced upon triggering by the pulse generator 366 in response to the s signal. The trailing edge of the timing signal of the timer 362 triggers the pulse generator 364 to strobe the entry timer 360 via the AND gate 368. Since a second input terminal of the AND gate 368 is coupled to the inverter 370, the entry timer 360 is activated in the absence of the g signal, the absence of the g signal designating the absence of activity by the mechanisms 114 and 116. During activity by the mechanisms 114 and 116, the g signal is present and, accordingly, the gate 368 inhibits activation of the timer 360.

Reviewing the functions provided by the timers, the prepare timer 332 operates the switch 328 to generate the y signal for strobing the comparators 154 (FIGS. 1,2) to read the input Y (precursor) signal. At the same time, the wait timer 384 operates the switch 374 to produce the s signal which is utilized in the foregoing timing functions, and also resets flip-flops in various units of the system 100 as has been described earlier. At the conclusion of the prepare interval, the readout timer 326 operates the switches 316 and 318 for driving reading current through the integrators, respectively, 142 and 144. As described previously, only the integrators 142 and 144 corresponding to a specific value of received Y signal would be readout in view of the connections of the lines 174A-C to respective ones of the switches 200A-C and 220A-C (FIGS. 1, 2, 4, 5 and 14). The entry of data by the timer 308 for the positive correlation occurs near the beginning of an operation interval, while the entry of data for the negative correlation by the timer 360 occurs near the end of the operation interval so as to allow time, by the allow timer 362, for the possible occurrence of the g signal.

In viewing the successive intervals of operation of the system 100, as portrayed in the diagrams of FIGS. 16–20, it is noted that the sequence of events is by way of example and that many other sequences of events are possible. It is also noted that the sequence of events varies from interval to interval, the variation due to responses of the patient 102 to the medications dispensed by the mechanisms 114 and 116. As has been noted earlier, the operation of the system 100 follows the human learning experience and, accordingly, as the system 100 learns, the foregoing sequence of events will change in accordance with the history of the patient's response as stored in the correlation storage unit 136 (FIG. 1).

For example, the signal v (FIGS. 1, 3, 7) from the signal processor 130 to the output timing circuit 128 immediately activates the second mechanism 116 to dispense medication at any instant in the operation of the system 100 when the blood pressure rises to the danger region. The v signal activates the timer 278 of the second mechanism 116. However, in the event that there has been previous positive correlation and, possibly, encouragement, then the timer 278 is activated by the AND gate 274 even though there may be no v and w signals due to the patient's blood pressure having dropped to a safe value. The AND gate 274 is activated by the signal on line 218 from the readout unit 146 (FIGS. 4, 14) and the signal coupled via the switch 292 (FIGS. 7,14) from the readout switch 316. The foregoing corresponds to the learning experience wherein additional doses of medicine are given to maintain a healthy condition in a patient.

As a further example, considering the case wherein negative correlation is present, the signal from the readout unit 148 (FIGS. 5,14) sets the flip-flop 222 which, via the inverter 198 (FIG. 3), applies a logic 0 to an input terminal of the AND gate 194. Thereby, the AND gates 190, 192 and 194 are all disabled so that the w signal is not provided even though the patient's blood pressure may be in the borderline region immediately below the threshold of the danger region. The foregoing example corresponds to the learning experience following a period of time wherein there has been little reinforcement or correlation, in which case the system 100 would not respond to merely one occurrence of a condition signal, X, in the borderline region. However, in the event that the blood pressure rose to the danger region, then the v signal would immediately activate the second mechanism 116.

Manual controls are provided to permit an attending physician to override the system 100 so as to prevent implementation of the mechanisms 114 and 116. Indicator lamps, not shown, may be provided on a control panel (not shown) to show a physician what portions of the system 100 are being activated. For example, lamps would be coupled to output terminals of the timers 278 and 280 to show the impending operations of the first and second mechanisms 114 and 116. In particular, the delays 282 and 284 of the output timing circuit 128 provide the attending physician with time to stop the mechanisms 114 and 116 before they are activated. The switch 352 (FIGS. 11, 15) on the u signal line which strobes the interval timer 340 may be opened manually to prevent the operation interval to be shortened by the activation of one of the mechanisms 114 and 116. The switch 292, coupling the timing circuitry to the AND gate 274 (FIGS. 7,14), may be manually opened to break the connection between the readout switch 316 and the AND gate 274 so as to prevent the output timing circuit 128 from reactivating the second mechanism 116 in response to stored data of the positive correlation.

Thereby, the system 100 adaptively controls the physiological condition of the patient by the use of a learning process patterned after the human learning experience, while permitting an attending physician to inject his own experience by overriding the operation of the system 100.

Referring now to FIGS. 21A–F, and in accordance with a further feature of the invention, the circuitry of the system 100 (FIG. 1) can be combined with other elements and additional ones of the systems 100 to provide networks 500A–F shown respectively in the FIGS. 21A–F. The networks 500A–E are multiple channel systems, wherein each channel incorporates a system 100, while the network 500F shows the use of a system 100 with a single input signal. The network 500A has three input terminals for receipt of X and Y signals and two output terminals for execution of mechanisms such as the mechanisms 114 and 116 of FIG. 1. The networks 500B-D have three input terminals and four output terminals. The network 500E has four input terminals and five output terminals.

Combination of two systems 100 is accomplished by connecting together the two X input terminals of the two systems 100 as in FIG. 21A, by connecting together the two Y input terminals as in FIG. 21D, by connecting an output terminal with a Y input terminal as in FIG. 21B, by connecting an output terminal with an X input terminal as in FIG. 21C, and by connecting together selected ones of the output terminals as in FIG. 21A. In addition, the signals at output terminals may be combined by further circuitry such as the AND gate 502 in FIG. 21E to provide executory signals for operation of mechanisms such as the mechanisms 114 and 116 of FIG. 1. In FIG. 21F, two threshold circuits 504 and 506 are coupled between a common input terminal 508 and, respectively, the X and Y input terminals of the system 100. The circuit 506 has a lower threshold than the circuit 504 so that the circuit 506 can couple an input signal from the terminal 508 to the Y input terminal of the system 100 even after such coupling has been stopped by the circuit 504 as when the input signal drops below the threshold of the circuit 504.

Figure 21L:
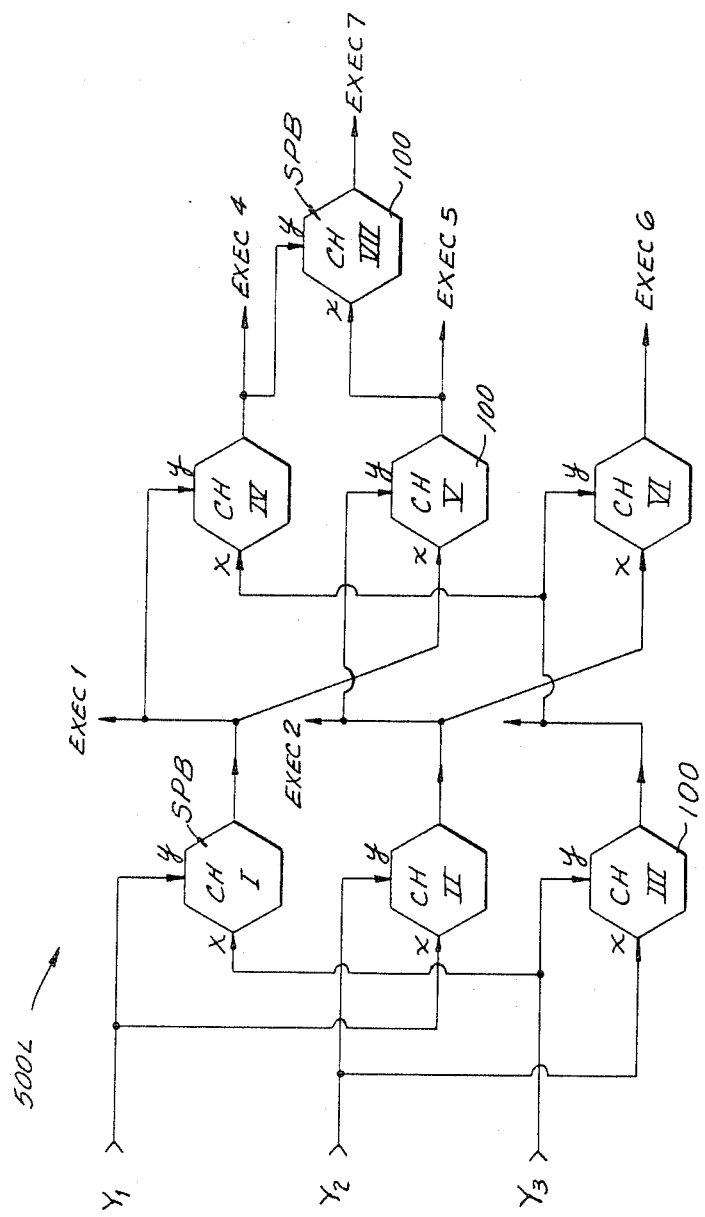

In FIGS. 21G-H, there are shown further networks 500G-H composed of multiple channels, each of which comprises three of the systems 100. The mode of interconnection of the three systems 100 follows that disclosed in the previous FIGS. 21A-E. In FIG. 21K, still more channels are provided in a network 500K comprising a total of seven of the systems 100. The first three channels, as well as the next three channels, are each connected according to the arrangement of FIG. 21G. The coupling of the third and the sixth channels to the seventh channel also follows the arrangement of FIG. 21G. In FIG. 21L, a further network 500L having seven channels is shown, each channel comprising a system 100. Output terminals of the first three channels are connected to input terminals of the next three channels by an interleaved arrangement.

By means of the foregoing networks 500A-L, and further networks (not shown) which can be constructed using the foregoing schemes of connection, adaptive control can be provided for more complex situations than can be handled by simply one of the systems 100. Such networks are constructed by using the system 100 as a basic building block. Such networks, or composite systems, are useful in the monitoring and treatment of complex biological phenomina. These networks provide for situations involving multiple precursor signals, multiple condition signals, and multiple output signals for the control of a multiplicity of the mechanisms 114 and 116 of FIG. 1.

It is to be understood that the above-described embodiment of the invention is illustrative only and that modifications thereof may occur to those skilled in the art. Accordingly, this invention is not to be regarded as limited to the embodiment disclosed herein, but is to be limited only as defined by the appended claims.

What is claimed is:

1. An adaptive control system providing an output signal in response to the reception, during a measurement interval, of a first input signal and a second input signal, the system comprising:

means for quantizing said first and said second input signals, each of said input signals being quantized into a plurality of ranges of values;

first and second sets of integrators corresponding to first and second ranges of values of said first input signal, individual ones of said integrators in each of said sets corresponding to respective ranges of values of said second input signal;

means for selecting one of said integrators corresponding to the joint occurrence, within said measurement interval, of a specific value range of said first input signal and a specific value range of said second input signal;

means for incrementing the amount of data stored in said one integrator upon said joint occurrence in the ranges of values of said first and said second input signals; and means for generating said output signal, said generating means being activated by said one integrator in response to the data stored therein.

2. A system according to claim 1 wherein said incrementing means provides both positive and negative increments to the data stored in said integrators.

3. A system according to claim 1 wherein said generating means is further activated by a first input signal having an amplitude falling in a higher one of said ranges of values.

4. A system according to claim 1 wherein said incrementing means includes punishment means for altering the sense of the incrementing from positive to negative, said punishment means comprising:

first means for signaling a repetition of values of said first input signal within a higher one of said ranges of values;

second means for signaling a repetition of values of said second input signal within the same range of values; and wherein said incrementing means decrements the data in said one integrator in response to the presence of a repetition signal from said second signaling means and the absence of a repetition signal from said first signaling means.

5. A system according to claim 1 wherein said generating means includes readout means coupled to said integrators for decrementing the data stored in said one integrator.

6. A system according to claim 4 wherein said generating means includes readout means coupled to said integrators for reading the data stored in said one integrator, said readout means decrementing the amount of said stored data during the reading of the data.

7. A system according to claim 1 wherein said one integrator is in said first set of integrators, and wherein said quantizing means provides a boderline range of values between said first and said second value ranges of said first input signal, said system further comprising logic means coupled to said incrementing means for activating said incrementing means in response to said first input signal having said borderline range of values in the absence of data in a second integrator of said second set, said second integrator corresponding to the same value range of said second input signal as said one integrator.

8. A system according to claim 7 further comprising means for delaying the incrementing of data in said second set of integrators until a later portion of said measurement interval subsequent to a period of time allocated for the incrementing of data in said first set of integrators.

9. A system according to claim 8 wherein said generating means provides a second output signal in response to an occurrence of said first input signal having an amplitude within said borderline range of values.

10. A system according to claim 6 further comprising sequencing means for triggering said quantizing means to provide a sample of said second input signal prior to the operation of said readout means.

11. A system according to claim 10 wherein said sequencing means includes a gating circuit for triggering the operation of said readout means in response to the occurrence of a sample of said second input signal.

12. A system according to claim 11 wherein said sequencing means resets said punishment means subsequent to said triggering of said quantizing means to permit the operation of said first and said second repetition signaling means.

13. A system according to claim 6 wherein the increment in data stored in any of said integrators due to the incrementing by said incrementing means is larger than the decrement in such data due to the decrementing by said readout means.

14. A system according to claim 4 further comprising means coupled to said punishment means for varying the magnitude of an increment in the negative sense relative to the magnitude of an increment in the positive sense.

15. A system according to claim 1 wherein said one integrator is in said first set of integrators, and wherein said one integrator and a second integrator in said second set correspond to the same value range of said second input signal, said quntizing means further providing a borderline range of values between said first and said second value ranges of first input signals, and said generating means further providing a second output signal in response to an occurrence of said borderline value of said first input signal, said system further comprising logic means coupling said borderline signal from said quantizing means to said generating means, said logic means being responsive to signals of said generating means and of said second integrator.

16. A system according to claim 15 wherein said logic means couples said borderline signal to said generating means only in the absence of an output signal from said generating means, said coupling by said logic means being further deactivated by the presence of data stored in said second integrator.

17. A system according to claim 16 wherein said logic means couples said borderline signal to said incrementing means, concurrently with the coupling of said borderline signal to said generating means, for incrementing data in said one integrator.

18. A system according to claim 17 wherein said logic means is activated by the presence of said second input signal in any of said ranges of value to provide said coupling of said borderline signal.

19. A system for the monitoring of the condition of a patient's health comprising:
means for sensing a precursor signal indicative of a future condition of the patient's health;
means for sensing a condition signal indicative of the present state of the patient's health;
means coupled to said precursor and said condition sensing means for storing individual ranges of values of said precursor signal occurring during an abnormal health condition;
means coupled to said storing means for incrementing a quantity of stored data upon successive occurrences of any one of said value ranges of said precursor signal;
repetition means for signaling a repetition of occurrence of any one of said value ranges of said precursor signal, said repetition means being coupled to said incrementing means for decrementing said quantity of stored data corresponding to any of said value ranges wherein a repetition has occurred in said precursor signal; and
generating means coupled to said storing means and said condition sensing means for generating an output signal, suitable for the activation of medicine delivery equipment, in response to the presence of stored data and the presence of an abnormal health condition.

20. A system according to claim 19 wherein said storing means includes a set of storage elements for the storing of individual ranges of values of said precursor signal occurring during a normal health condition, said condition sensing means providing a borderline signal in response to a condition signal designating a borderline condition between the normal and the abnormal conditions of health, and wherein said system further comprises logic means coupling said borderline signal to said generating means in the absence of a quantity of stored data for the normal health condition and a specific range of values of said precursor signal.

21. A system according to claim 20 wherein said generating means generates a second output signal in response to said borderline signal, said second output signal being suitable for the activation of medicine delivery equipment.

22. A system according to claim 21 wherein said logic means decouples said borderline signal from said generating means in the presence of an output signal from said generating means.

23. A system according to claim 19 wherein said repetition means includes logic means responsive to the sensing, by the sensing means, of an abnormal health condition for inhibiting said decrementing during said abnormal health condition, 24. A system according to claim 19 further comprising timing means for operating said precursor sensing means at regular intervals for providing samples of said precursor signal during the absence of an output signal from said generating means, said generating means applying signals to said timing means for inhibiting the recycling of said timing means during the generation of an output signal, said generating means restarting said timing means at the conclusion of the generation of an output signal.

25. A system according to claim 24 wherein said timing means includes sequencing means, said system further comprising readout means coupled between said storing means and said generating means for reading data stored in said storing means, said readout means including a comparator and threshold circuitry for signaling said generating means upon the stored data exceeding the threshold, the readout means being activated by the sequencing means subsequent to the providing of samples of precursor signals by the precursor sensing means.

26. A system according to claim 25 wherein the incremental changes in said stored data resulting from said decrementing are smaller than the incremental changes in said stored data resulting from said incrementing.

* * * * *